(12) United States Patent
Iguchi et al.

(10) Patent No.: US 9,045,799 B2
(45) Date of Patent: Jun. 2, 2015

(54) PROBE FOR DETECTING POLYMORPHISM IN CYP3A GENE, METHOD OF DETECTING POLYMORPHISM, METHOD OF EVALUATING DRUG EFFICACY, AND REAGENT KIT FOR DETECTING POLYMORPHISM

(75) Inventors: Aki Iguchi, Kyoto (JP); Mitsuharu Hirai, Kyoto (JP)

(73) Assignee: ARKRAY, Inc., Kyoto (JP)

( * ) Notice: Subject to any disclaimer, the term of this patent is extended or adjusted under 35 U.S.C. 154(b) by 0 days.

(21) Appl. No.: 13/416,357

(22) Filed: Mar. 9, 2012

(65) Prior Publication Data

US 2012/0270215 A1    Oct. 25, 2012

(30) Foreign Application Priority Data

Mar. 9, 2011 (JP) ................................ 2011-051631

(51) Int. Cl.
*C12Q 1/68* (2006.01)
*C12P 19/34* (2006.01)
*C07H 21/02* (2006.01)

(52) U.S. Cl.
CPC ............ *C12Q 1/6883* (2013.01); *C12Q 1/6876* (2013.01); *C12Q 2600/112* (2013.01); *C12Q 2600/156* (2013.01)

(58) Field of Classification Search
CPC ............... C12Q 1/6883; C12Q 1/6876; C12Q 2600/112; C12Q 2600/156
See application file for complete search history.

(56) References Cited

U.S. PATENT DOCUMENTS

| 4,889,818 | A | 12/1989 | Gelfand et al. |
| 5,079,352 | A | 1/1992 | Gelfand et al. |
| 7,354,707 | B2 | 4/2008 | Kurane et al. |
| 2006/0172334 | A1 | 8/2006 | Wilke et al. |
| 2009/0075254 | A1 | 3/2009 | Ruano et al. |

FOREIGN PATENT DOCUMENTS

| EP | 1295941 A1 | 3/2003 |
| JP | 2002-119291 A | 4/2002 |
| WO | 91/09950 A1 | 7/1991 |
| WO | 92/09689 A1 | 6/1992 |
| WO | 2006/075254 A2 | 7/2006 |
| WO | 2009/026116 A2 | 2/2009 |

OTHER PUBLICATIONS

Gjerde et al. BMC Cancer 2010, 10:313, pp. 1-13.*
Tanaka R. et al. Leukemia Research 32 (2008), 1462-1467.*
Fukushima-Uesaka et al., "Haplotypes of CYP3A4 and Their Close Linkage With CYP3A5 Haplotypes in a Japanese Population," Human Mutation. 2004, vol. 23, Issue 1, p. 100.
Nakajima et al., "Impact of the haplotype CYP3A4*16B harboring the Thr185Ser substitution on paclitaxel metabolism in Japanese patients with cancer," Clin. Pharmacol. Ther., 2006, vol. 80, pp. 179-191 [Abstract only].
Taheri et al., "Effect of MDR1 polymorphism on multidrug resistance expression in breast cancer patients," Genet. Mol. Res., 2010, vol. 9, No. 1, pp. 34-40.
Partial Search Report issued in corresponding European Patent Application No. 12158915.4 dated Jun. 6, 2012.
Kivisto et al., "Lipid-lowering response to statins is affected by CYP3A5 polymorphism," Pharmacogenetics, 14: 523-525 (2004).
Dally et al., "Genotype relationships in the CYP3A locus in Caucasians," Cancer Letters, 207: 95-99 (2004).
Cheung et al., "Influence of different allelic variants of the CYP3A and ABCB1 genes on the tacrolimus pharmacokinetic profile of Chinese renal transplant recipiants," Pharmacogenomics, 7: 563-574 (2006).
Database accession No. AWP06896 retrieved from EBI.
Database accession No. AWI87600 retrieved from EBI.
Nakajima et al., "Impact of the haplotype CYP3A46*16B harboring the Thr185Ser substitution on paclitaxel metabolism in Japanese patients with cancer," Clin. Pharmacol. Ther., 2006, vol. 80, pp. 179-191.
Office Action issued in corresponding European Patent Application No. 12158915.4 dated Sep. 9, 2013.
Office Action issued in corresponding European Patent Application No. 12158915.4 dated Aug. 4, 2014.

* cited by examiner

*Primary Examiner* — Stephen Kapushoc
(74) *Attorney, Agent, or Firm* — Morgan, Lewis & Bockius LLP

(57) ABSTRACT

Provided in the present disclosure is a probe for detecting polymorphism that enables a simple detection of polymorphism in the CYP3A gene with high sensitivity.

21 Claims, 5 Drawing Sheets

SEQUENCE LISTING

<160> NUMBER OF SEQ ID NOS: 45

<210> SEQ ID NO 1
<211> LENGTH: 801
<212> TYPE: DNA
<213> ORGANISM: Homo sapiens

<400> SEQUENCE: 1
tttgttcact agaagcaagt gggagaaagc tttgcctctt tgtacttctt catcttctcc     60

| | | |
|---|---|---|
| cctcaagtcc tcagaatcca cagcgctgac tgtggagtgc tgtggagctg gcatggccca | 120 | |
| tacaggcaac atgacttagt agacagatga cacagctcta gatgtccatg ggccccacac | 180 | |
| caactgccct tgcagcattt agtccttgtg agcacttgat gatttacctg ccttcaattt | 240 | |
| ttcactgacc taatattctt tttgataatg aagtatttta aacatataaa acattatgga | 300 | |
| gagtggcata ggagataccc acgtatgtac cacccagctt aacgaatgct ctactgtcat | 360 | |
| ttctaaccat aatctcttta aagagctctt ttgtctttca rtatctcttc cctgtttgga | 420 | |
| ccacattacc cttcatcata tgaagccttg ggtggctcct gtgtgagact cttgctgtgt | 480 | |
| gtcacaccct aatgaactag aacctaaggt tgctgtgtgt cgtacaacta ggggtatgga | 540 | |
| ttacataaca taatgatcaa agtctggctt cctgggtgtg gctccagctg cagaatcggg | 600 | |
| ctagtgaagt ttaatcagct ccgttgtccc cacacagaac gtatgaaggt caactccctg | 660 | |
| tgctggccat cacagatccc gacgtgatca gaacagtgct agtgaaagaa tgttattctg | 720 | |
| tcttcacaaa tcgaagggta agcatccatt ttttgaaatt taaataatga ttgatccact | 780 | |
| gattaaattt ttattttgaa a | 801 | |

<210> SEQ ID NO 2
<211> LENGTH: 410
<212> TYPE: DNA
<213> ORGANISM: Homo sapiens

<400> SEQUENCE: 2

| | | |
|---|---|---|
| cacctgataa caccttctga tggagtgtga tagaaggtga tctagtagat ctgaaagtct | 60 | |
| gtggctgttt gtctgtcttg actggacatg tgggtttcct gttgcatgca tagaggaagg | 120 | |
| atggtaaaaa ggtgctgatt ttaattttcc acatctttct ccactcagcg tctttggggc | 180 | |
| ctacagcatg gatgtgatca stagcwcatc atytggagtg aacrtygact ctctcaacaa | 240 | |
| tccacaagac cccttgtgg aaaacaccaa gaagctttta agatttgatt ttttggatcc | 300 | |
| attcttctc tcaataagta tgtggactac tatttccttt watttatctt kctctcttaa | 360 | |
| aaataactgc tttattgaga yataaatcac catgtaattc atccacttaa | 410 | |

<210> SEQ ID NO 3
<211> LENGTH: 701
<212> TYPE: DNA
<213> ORGANISM: Homo sapiens

<400> SEQUENCE: 3

| | | |
|---|---|---|
| cagctgaggc acagccaaga gctctggctg tattaatgac ctaagaagtc accagaaagt | 60 | |
| cagaagggat gacatgcaga ggcccagcaa tctcagctaa gtcaactcca ccagcctttc | 120 | |
| tagttgccca ctgtgtgtac agcacccctgg tagggaccag agccatgaca gggaataaga | 180 | |
| ctagactatg cccttgagga gctcacctct gttcagggaa acaggcgtgg aaacacaatg | 240 | |
| gtggtaaaga ggaaagagga caataggatt gcatgaaggg gatggaaagt gcccagggga | 300 | |
| ggaaatggtt acatctgtgt gaggagtttg gtgaggaaag actctaagag aaggctctgt | 360 | |
| ctgtctgggt ttggaaggat gtgtaggagt cttctagggg gcacaggcac actccaggca | 420 | |
| taggtaaaga tctgtaggtg tggcttgttg ggatgaattt caagtatttt ggaatgagga | 480 | |
| cagccataga grcaagggca rgagagvggc gatttaatag atttatgcc aatggctcca | 540 | |
| cttgagtttc tgataagaac ccagaaccct tggactcccc agtaacattg attgagttgt | 600 | |
| ttatgatacc tcatagaata tgaactcaaa ggaggtcagt gagtggtgtg tgtgtgattc | 660 | |
| tttgccaact tccaaggtgg agaagcctct tccaactgca g | 701 | |

```
<210> SEQ ID NO 4
<211> LENGTH: 21
<212> TYPE: DNA
<213> ORGANISM: Artificial
<220> FEATURE:
<223> OTHER INFORMATION: probe

<400> SEQUENCE: 4
ttgtctttca gtatctcttc c                                              21

<210> SEQ ID NO 5
<211> LENGTH: 21
<212> TYPE: DNA
<213> ORGANISM: Artificial
<220> FEATURE:
<223> OTHER INFORMATION: probe

<400> SEQUENCE: 5
ttgtctttca atatctcttc c                                              21

<210> SEQ ID NO 6
<211> LENGTH: 15
<212> TYPE: DNA
<213> ORGANISM: Artificial
<220> FEATURE:
<223> OTHER INFORMATION: probe

<400> SEQUENCE: 6
gatgtgatca gtagc                                                     15

<210> SEQ ID NO 7
<211> LENGTH: 15
<212> TYPE: DNA
<213> ORGANISM: Artificial
<220> FEATURE:
<223> OTHER INFORMATION: probe

<400> SEQUENCE: 7
gatgtgatca ctagc                                                     15

<210> SEQ ID NO 8
<211> LENGTH: 19
<212> TYPE: DNA
<213> ORGANISM: Artificial
<220> FEATURE:
<223> OTHER INFORMATION: probe

<400> SEQUENCE: 8
tgtgctactg atcacatcc                                                 19

<210> SEQ ID NO 9
<211> LENGTH: 21
<212> TYPE: DNA
<213> ORGANISM: Artificial
<220> FEATURE:
<223> OTHER INFORMATION: probe

<400> SEQUENCE: 9
ctactgatca catccatgct g                                              21

<210> SEQ ID NO 10
<211> LENGTH: 27
<212> TYPE: DNA
<213> ORGANISM: Artificial
<220> FEATURE:
```

```
<223> OTHER INFORMATION: probe

<400> SEQUENCE: 10
atgatgtgct actgatcaca tccatgc                                          27

<210> SEQ ID NO 11
<211> LENGTH: 25
<212> TYPE: DNA
<213> ORGANISM: Artificial
<220> FEATURE:
<223> OTHER INFORMATION: probe

<400> SEQUENCE: 11
gatgtgctag tgatcacatc catgc                                            25

<210> SEQ ID NO 12
<211> LENGTH: 21
<212> TYPE: DNA
<213> ORGANISM: Artificial
<220> FEATURE:
<223> OTHER INFORMATION: probe

<400> SEQUENCE: 12
taaatcgccg ctctcctgcc c                                                21

<210> SEQ ID NO 13
<211> LENGTH: 21
<212> TYPE: DNA
<213> ORGANISM: Artificial
<220> FEATURE:
<223> OTHER INFORMATION: probe

<400> SEQUENCE: 13
taaatcgccg ctctcttgcc c                                                21

<210> SEQ ID NO 14
<211> LENGTH: 23
<212> TYPE: DNA
<213> ORGANISM: Artificial
<220> FEATURE:
<223> OTHER INFORMATION: primer

<400> SEQUENCE: 14
cgtatgtacc acccagctta acg                                              23

<210> SEQ ID NO 15
<211> LENGTH: 18
<212> TYPE: DNA
<213> ORGANISM: Artificial
<220> FEATURE:
<223> OTHER INFORMATION: primer

<400> SEQUENCE: 15
cacaggagcc acccaagg                                                    18

<210> SEQ ID NO 16
<211> LENGTH: 20
<212> TYPE: DNA
<213> ORGANISM: Artificial
<220> FEATURE:
<223> OTHER INFORMATION: primer

<400> SEQUENCE: 16
aggatggtaa aaaggtgctg                                                  20
```

```
<210> SEQ ID NO 17
<211> LENGTH: 21
<212> TYPE: DNA
<213> ORGANISM: Artificial
<220> FEATURE:
<223> OTHER INFORMATION: primer

<400> SEQUENCE: 17
gagagaaaga atggatccaa a                                            21

<210> SEQ ID NO 18
<211> LENGTH: 33
<212> TYPE: DNA
<213> ORGANISM: Artificial
<220> FEATURE:
<223> OTHER INFORMATION: primer

<400> SEQUENCE: 18
ctagaggagt gtgatagaag gtgatctagt aga                               33

<210> SEQ ID NO 19
<211> LENGTH: 50
<212> TYPE: DNA
<213> ORGANISM: Artificial
<220> FEATURE:
<223> OTHER INFORMATION: oligonucleotide

<400> SEQUENCE: 19
ttcactccar atgatgtgct actgatcaca tccatgctgt aggccccaaa             50

<210> SEQ ID NO 20
<211> LENGTH: 50
<212> TYPE: DNA
<213> ORGANISM: Artificial
<220> FEATURE:
<223> OTHER INFORMATION: oligonucleotide

<400> SEQUENCE: 20
ttcactccar atgatgtgct agtgatcaca tccatgctgt aggccccaaa             50

<210> SEQ ID NO 21
<211> LENGTH: 50
<212> TYPE: DNA
<213> ORGANISM: Artificial
<220> FEATURE:
<223> OTHER INFORMATION: oligonucleotide

<400> SEQUENCE: 21
tttggggcct acagcatgga tgtgatcagt agcacatcat ytggagtgaa             50

<210> SEQ ID NO 22
<211> LENGTH: 50
<212> TYPE: DNA
<213> ORGANISM: Artificial
<220> FEATURE:
<223> OTHER INFORMATION: oligonucleotide

<400> SEQUENCE: 22
tttggggcct acagcatgga tgtgatcact agcacatcat ytggagtgaa             50

<210> SEQ ID NO 23
<211> LENGTH: 50
<212> TYPE: DNA
<213> ORGANISM: Artificial
<220> FEATURE:
<223> OTHER INFORMATION: oligonucleotide
```

-continued

<400> SEQUENCE: 23
taaagagctc ttttgtcttt caatatctct tccctgtttg gaccacatta          50

<210> SEQ ID NO 24
<211> LENGTH: 50
<212> TYPE: DNA
<213> ORGANISM: Artificial
<220> FEATURE:
<223> OTHER INFORMATION: oligonucleotide

<400> SEQUENCE: 24
taaagagctc ttttgtcttt cagtatctct tccctgtttg gaccacatta          50

<210> SEQ ID NO 25
<211> LENGTH: 22
<212> TYPE: DNA
<213> ORGANISM: Artificial
<220> FEATURE:
<223> OTHER INFORMATION: probe

<400> SEQUENCE: 25
cagggaagag atactgaaag ac          22

<210> SEQ ID NO 26
<211> LENGTH: 26
<212> TYPE: DNA
<213> ORGANISM: Artificial
<220> FEATURE:
<223> OTHER INFORMATION: primer

<400> SEQUENCE: 26
ctgtaggtgt ggcttgttgg gatgaa          26

<210> SEQ ID NO 27
<211> LENGTH: 31
<212> TYPE: DNA
<213> ORGANISM: Artificial
<220> FEATURE:
<223> OTHER INFORMATION: primer

<400> SEQUENCE: 27
ggagccattg gcataaaatc tattaaatcg c          31

<210> SEQ ID NO 28
<211> LENGTH: 26
<212> TYPE: DNA
<213> ORGANISM: Artificial
<220> FEATURE:
<223> OTHER INFORMATION: primer

<400> SEQUENCE: 28
gacgagagag aaagaatgga tccaaa          26

<210> SEQ ID NO 29
<211> LENGTH: 40
<212> TYPE: DNA
<213> ORGANISM: Artificial
<220> FEATURE:
<223> OTHER INFORMATION: oligonucleotide

<400> SEQUENCE: 29
agccatagag acaagggcaa gagagggcg atttaataga          40

<210> SEQ ID NO 30
<211> LENGTH: 40

```
<212> TYPE: DNA
<213> ORGANISM: Artificial
<220> FEATURE:
<223> OTHER INFORMATION: oligonucleotide

<400> SEQUENCE: 30
agccatagag acaagggcag gagagaggcg atttaataga                          40

<210> SEQ ID NO 31
<211> LENGTH: 40
<212> TYPE: DNA
<213> ORGANISM: Artificial
<220> FEATURE:
<223> OTHER INFORMATION: oligonucleotide

<400> SEQUENCE: 31
agccatagag acaagggcag gagaggggcg atttaataga                          40

<210> SEQ ID NO 32
<211> LENGTH: 15
<212> TYPE: DNA
<213> ORGANISM: Artificial
<220> FEATURE:
<223> OTHER INFORMATION: probe

<400> SEQUENCE: 32
ctctcttgcc cttgt                                                     15

<210> SEQ ID NO 33
<211> LENGTH: 40
<212> TYPE: DNA
<213> ORGANISM: Artificial
<220> FEATURE:
<223> OTHER INFORMATION: oligonucleotide

<400> SEQUENCE: 33
tctattaaat cgcccctctc ttgcccttgt ctctatggct                          40

<210> SEQ ID NO 34
<211> LENGTH: 40
<212> TYPE: DNA
<213> ORGANISM: Artificial
<220> FEATURE:
<223> OTHER INFORMATION: oligonucleotide

<400> SEQUENCE: 34
tctattaaat cgcctctctc ctgcccttgt ctctatggct                          40

<210> SEQ ID NO 35
<211> LENGTH: 40
<212> TYPE: DNA
<213> ORGANISM: Artificial
<220> FEATURE:
<223> OTHER INFORMATION: oligonucleotide

<400> SEQUENCE: 35
tctattaaat cgcccctctc ctgcccttgt ctctatggct                          40

<210> SEQ ID NO 36
<211> LENGTH: 16
<212> TYPE: DNA
<213> ORGANISM: Artificial
<220> FEATURE:
<223> OTHER INFORMATION: probe

<400> SEQUENCE: 36
```
caagggcaag agagag                                           16

<210> SEQ ID NO 37
<211> LENGTH: 21
<212> TYPE: DNA
<213> ORGANISM: Artificial
<220> FEATURE:
<223> OTHER INFORMATION: probe

<400> SEQUENCE: 37
ttgtctttca rtatctcttc c                                     21

<210> SEQ ID NO 38
<211> LENGTH: 15
<212> TYPE: DNA
<213> ORGANISM: Artificial
<220> FEATURE:
<223> OTHER INFORMATION: probe

<400> SEQUENCE: 38
gatgtgatca stagc                                            15

<210> SEQ ID NO 39
<211> LENGTH: 19
<212> TYPE: DNA
<213> ORGANISM: Artificial
<220> FEATURE:
<223> OTHER INFORMATION: probe

<400> SEQUENCE: 39
tgtgctastg atcacatcc                                        19

<210> SEQ ID NO 40
<211> LENGTH: 19
<212> TYPE: DNA
<213> ORGANISM: Artificial
<220> FEATURE:
<223> OTHER INFORMATION: probe

<400> SEQUENCE: 40
tgtgctagtg atcacatcc                                        19

<210> SEQ ID NO 41
<211> LENGTH: 27
<212> TYPE: DNA
<213> ORGANISM: Artificial
<220> FEATURE:
<223> OTHER INFORMATION: probe

<400> SEQUENCE: 41
atgatgtgct astgatcaca tccatgc                               27

<210> SEQ ID NO 42
<211> LENGTH: 27
<212> TYPE: DNA
<213> ORGANISM: Artificial
<220> FEATURE:
<223> OTHER INFORMATION: probe

<400> SEQUENCE: 42
atgatgtgct agtgatcaca tccatgc                               27

<210> SEQ ID NO 43
<211> LENGTH: 25
<212> TYPE: DNA
<213> ORGANISM: Artificial

```
<220> FEATURE:
<223> OTHER INFORMATION: probe

<400> SEQUENCE: 43
gatgtgctas tgatcacatc catgc                                              25

<210> SEQ ID NO 44
<211> LENGTH: 25
<212> TYPE: DNA
<213> ORGANISM: Artificial
<220> FEATURE:
<223> OTHER INFORMATION: probe

<400> SEQUENCE: 44
gatgtgctac tgatcacatc catgc                                              25

<210> SEQ ID NO 45
<211> LENGTH: 21
<212> TYPE: DNA
<213> ORGANISM: Artificial
<220> FEATURE:
<223> OTHER INFORMATION: probe

<400> SEQUENCE: 45
taaatcgccg ctctcytgcc c                                                  21
```

PROBE FOR DETECTING POLYMORPHISM IN CYP3A GENE, METHOD OF DETECTING POLYMORPHISM, METHOD OF EVALUATING DRUG EFFICACY, AND REAGENT KIT FOR DETECTING POLYMORPHISM

CROSS-REFERENCE TO RELATED APPLICATION

This application claims priority from Japanese Patent Application No. 2011-051631 filed on Mar. 9, 2011. The entire subject matter of the Japanese Patent Application is incorporated herein by reference in its entirety.

SEQUENCE LISTING SUBMISSION VIA EFS-WEB

A computer readable text file, entitled "SequenceListing.txt," created on or about Mar. 5, 2012 with a file size of about 10 kb contains the sequence listing for this application and is hereby incorporated by reference in its entirety.

BACKGROUND OF THE INVENTION

The present invention relates to a probe for detecting polymorphism in the CYP3A gene, a method of use (e.g. a method of detecting polymorphism, a method of evaluating a drug efficacy), and a reagent kit for detecting polymorphism.

CYP (Cytochrome P450) is an oxidase involved in metabolism of a biological material such as steroid hormone and an oxidative detoxification reaction of a drug, an environmental pollutant, or the like. CYP forms a superfamily including a multitude of molecular species. Among them, CYP3A4 and CYP3A5 are known for containing polymorphism affecting metabolism of a medicine, for example (Human Mutation, 2004, Vol. 23, Issue 1, pp. 100 to 108).

The CYP3A5 gene encoding CYP3A5 is located in human chromosome 7. For example, with respect to the 401st base (r) in a partial sequence (SEQ ID NO: 1) of the CYP3A5 gene, a mutation (CYP3A5*3) from adenine (a) to guanine (g) is known (Clin. Pharmacol. Ther., 2006, Vol. 80, pp. 179 to 191, etc.). This base mutation causes an abnormal splicing, and the expression of CYP3A5 decreases greatly.

Further, the CYP3A4 gene encoding CYP3A4 is located in human chromosome 7. For example, with respect to the 201st base(s) in a partial sequence (SEQ ID NO: 2) of the CYP3A4 gene, a mutation (CYP3A4*16) from cytosine (c) to guanine (g) is known (Clin. Pharmacol. Ther., 2006, Vol. 80, pp. 179 to 191, etc.). By this base mutation, the 185th threonine (T) of CYP3A4 is mutated to serine (S).

It has been reported that these mutations have an association with, for example, metabolism of a drug such as the immunosuppressant, tacrolimus (Clin. Pharmacol. Ther., 2006, Vol. 80, pp. 179 to 191). Therefore, it is considered that there is a possibility of enabling the prediction of a tolerance to a drug with higher sensitivity by detecting these polymorphisms in the CYP3A gene.

Currently, for example, a polymerase chain reaction (PCR)-restriction fragment length polymorphism (RFLP) method is known as a method of detection polymorphism in a gene (Genet. Mol. Res., 2010, Vol. 9, Issue 1, pp. 34 to 40). In this method, PCR is performed using a primer that is designed so as to amplify a section containing a base to be detected, an amplification product is cleaved with a restriction enzyme that cleaves or not cleaves depending on the presence or absence of the mutation in the specific bases, and the determination of whether or not the section has been cleaved is performed by electrophoresis.

Further, the following method is also known. That is, in the method, a region containing mutation is amplified by a PCR method, then a melting curve analysis is performed using a nucleic acid probe labeled with a fluorescent dye, and mutation in a base sequence is analyzed based on the result of the melting curve analysis as described in JP 2002-119291 A or the like.

BRIEF SUMMARY OF THE INVENTION

However, as described above, there are various mutations in the CYP3A gene. The PCR-RFLP method needs to apply a restriction enzyme treatment to an amplification product taken out after a PCR reaction. Therefore, there is a possibility that a next reaction system is contaminated with the amplification product, and this may cause the results of false-positive and false-negative. Further, since treatment is performed with a restriction enzyme after completion of PCR and electrophoresis is performed thereafter, there is a case that a quite long time is required until the determination is completed. Moreover, since the PCR-RFLP method requires complicated operations, the automatization thereof is difficult. On the basis of these current circumstances, a further development of technologies for detecting polymorphism in the CYP3A gene has been awaited.

In one aspect, the present invention is intended to provide a probe for detecting polymorphism that enables a simple detection of polymorphism in the CYP3A gene with high sensitivity; and a method of detecting polymorphism using the probe. Further, in another aspect, the present invention is intended to provide a method of evaluating a drug efficacy using the method of detecting polymorphism. Furthermore, in yet another aspect, the present invention is intended to provide a reagent kit for detecting polymorphism using the probe for detecting polymorphism.

A probe according to some embodiments of the present invention includes one oligonucleotide selected from the group consisting of oligonucleotides P1, P1', P2, P2', P3, P3', P4, P4', P5, and P5', wherein P1 is an oligonucleotide having a sequence including the 401st to the 411th bases of SEQ ID NO: 1 and having a length of from 11 bases to 50 bases, the sequence having at least 85% identity to the 401st to the 411th bases of SEQ ID NO: 1 with the exception that the base corresponding to the 411th base in SEQ ID NO: 1 is cytosine411th;

P1' is an oligonucleotide having a sequence including the 401st to the 411th bases of SEQ ID NO: 1 and having a length of from 11 bases to 50 bases, the sequence being hybridized under stringent conditions to a complementary strand of the 401st to the 411th bases of SEQ ID NO: 1 with the exception that the base corresponding to the 411th base in SEQ ID NO: 1 is cytosine411th;

P2 is an oligonucleotide having a sequence including the 201st to the 205th bases of SEQ ID NO: 2 and having a length of from 5 bases to 50 bases, the sequence having at least 85% identity to the 201st to the 205th bases of SEQ ID NO: 2 with the exception that the base corresponding to the 205th base in SEQ ID NO: 2 is cytosine;

P2' is an oligonucleotide having a sequence including the 201st to the 205th bases of SEQ ID NO: 2 and having a length of from 5 bases to 50 bases, the sequence being hybridized under stringent conditions to a complementary strand of the 201st to the 205th bases of SEQ ID NO: 2 with the exception that the base corresponding to the 205th base in SEQ ID NO: 2 is cytosine;

P3 is an oligonucleotide having a sequence complementary to a sequence including the 190th to the 201st bases of SEQ ID NO: 2 and having a length of from 12 bases to 50 bases, the sequence having at least 85% identity to the 190th to the 201st bases of a complementary strand of SEQ ID NO: 2 with the exception that the base complementary to the 190th base in SEQ ID NO: 2 is cytosine;

P3' is an oligonucleotide having a sequence complementary to a sequence including the 190th to the 201st bases of SEQ ID NO: 2 and having a length of from 12 bases to 50 bases, the sequence being hybridized under stringent conditions to the 190th to the 201st bases of SEQ ID NO: 2 with the exception that the base complementary to the 190th base in SEQ ID NO: 2 is cytosine;

P4 is an oligonucleotide having a sequence complementary to a sequence including the 186th to the 201st bases of SEQ ID NO: 2 and having a length of from 16 bases to 50 bases, the sequence having at least 85% identity to the 186th to the 201st bases of a complementary strand of SEQ ID NO: 2 with the exception that the base complementary to the 186th base in SEQ ID NO: 2 is cytosine;

P4' is an oligonucleotide having a sequence complementary to a sequence including the 186th to the 201st bases of SEQ ID NO: 2 and having a length of from 16 bases to 50 bases, the sequence being hybridized under stringent conditions to the 186th to the 201st bases of SEQ ID NO: 2 with the exception that the base complementary to the 186th base in SEQ ID NO: 2 is cytosine;

P5 is an oligonucleotide having a sequence complementary to a sequence including the 496th to the 501st bases of SEQ ID NO: 3 and having a length of from 6 bases to 50 bases, the sequence having at least 85% identity to the 496th to the 501st bases of a complementary strand of SEQ ID NO: 3 with the exception that the base complementary to the 496th base in SEQ ID NO: 3 is cytosine; and P5' is an oligonucleotide having a sequence complementary to a sequence including the 496th to the 501st bases of SEQ ID NO: 3 and having a length of from 6 bases to 50 bases, the sequence being hybridized under stringent conditions to the 496th to the 501st bases of SEQ ID NO: 3 with the exception that the base complementary to the 496th base in SEQ ID NO: 3 is cytosine.

In some embodiments, the probe described herein may be labeled. In further embodiments, the probe may be fluorescence-labeled. In additional embodiments, the fluorescently labeled probe emits fluorescence when not hybridized to its target sequence, and the fluorescence intensity of the fluorescently labeled oligonucleotide when hybridized to its target sequence is larger or smaller than the fluorescence intensity when not hybridized to its target sequence. In yet additional embodiments, the fluorescently labeled probe emits fluorescence when not hybridized to its target sequence, and the fluorescence intensity of the fluorescently labeled oligonucleotide when hybridized to its target sequence is smaller than the fluorescence intensity when not hybridized to its target sequence.

In one aspect, in the oligonucleotide P1, the base corresponding to the 411th base of SEQ ID NO: 1 is labeled with a fluorescent dye; in the oligonucleotide P1', the base corresponding to the 411th base of SEQ ID NO: 1 being labeled with a fluorescent dye; in the oligonucleotide P2, the base corresponding to the 205th base of SEQ ID NO: 2 being labeled with a fluorescent dye; in the oligonucleotide P2', the base corresponding to the 205th base of SEQ ID NO: 2 being labeled with a fluorescent dye; in the oligonucleotide P3, the base complementary to the 190th base of SEQ ID NO: 2 being labeled with a fluorescent dye; in the oligonucleotide P3', the base complementary to the 190th base of SEQ ID NO: 2 being labeled with a fluorescent dye; in the oligonucleotide P4, the base complementary to the 186th base of SEQ ID NO: 2 being labeled with a fluorescent dye; in the oligonucleotide P4', the base complementary to the 186th base of SEQ ID NO: 2 being labeled with a fluorescent dye; in the oligonucleotide P5, the base complementary to the 496th base of SEQ ID NO: 3 being labeled with a fluorescent dye; and/or in the oligonucleotide P5', the base complementary to the 496th base of SEQ ID NO: 3 being labeled with a fluorescent dye.

In another aspect, the oligonucleotides P1, P1', P2, P2', P3, P3', P4, P4', P5, and P5' recognize a polymorphism of the 401st base in SEQ ID NO: 1.

In another aspect, the oligonucleotides P1, P1', P2, P2', P3, P3', P4, P4', P5, and P5'are labeled at a position of any one of 1st to 3rd positions from the 3' end of the oligonucleotides.

In another aspect, the oligonucleotides P1, P1', P2, P2', P3, P3', P4, P4', P5, and P5'are labeled at the 3' end of the oligonucleotides.

In some embodiments, the oligonucleotide P1 and the oligonucleotide P1' each have a length of from 15 bases to 30 bases, the oligonucleotide P2 and the oligonucleotide P2' each have a length of from 10 bases to 30 bases, the oligonucleotide P3 and the oligonucleotide P3' each have a length of from 12 bases to 40 bases, the oligonucleotide P4 and the oligonucleotide P4' each have a length of from 16 bases to 40 bases, and/or the oligonucleotide P5 and the oligonucleotide P5' each have a length of from 10 bases to 40 bases.

In additional embodiments, the oligonucleotide P1 and the oligonucleotide P1' each have a length of from 15 bases to 20 bases, the oligonucleotide P2 and the oligonucleotide P2' each have a length of from 10 bases to 20 bases, the oligonucleotide P3 and the oligonucleotide P3' each have a length of from 15 bases to 30 bases, the oligonucleotide P4 and the oligonucleotide P4' each have a length of from 20 bases to 30 bases, and/or the oligonucleotide P5 and the oligonucleotide P5' each have a length of from 20 bases to 30 bases.

In one aspect, the probe described herein comprises a base sequence of SEQ ID NO: 37, SEQ ID NO: 38, SEQ ID NO: 39, SEQ ID NO: 41, SEQ ID NO: 43, or SEQ ID NO: 45. In another aspect, the probe described herein comprises a base sequence of SEQ ID NO: 4, SEQ ID NO: 6, SEQ ID NO: 8, SEQ ID NO: 10, SEQ ID NO: 44, or SEQ ID NO: 12. In another aspect, the probe consists of a base sequence of SEQ ID NO: 37, SEQ ID NO: 38, SEQ ID NO: 39, SEQ ID NO: 41, SEQ ID NO: 43, or SEQ ID NO: 45. In another aspect, the probe consists of SEQ ID NO: 4, SEQ ID NO: 6, SEQ ID NO: 8, SEQ ID NO: 10, SEQ ID NO: 44, or SEQ ID NO: 12.

The present invention according to some embodiments includes a method of detecting polymorphism in a CYP3A gene in a sample using the probe described herein, comprising adding to the sample the probe according to claim 1, obtaining a melting curve for the probe, and determining the melting temperature of the probe from the melting curve, wherein the melting temperature indicates the presence of the polymorphism in the CYP3A gene. In some embodiments, the method may further comprise contacting the probe with a single-stranded nucleic acid in a sample and hybridizing the probe and the single-stranded nucleic acid to obtain a hybrid; measuring a change in a fluorescent signal based on dissociation of the hybrid by changing the temperature of the sample comprising the hybrid in order to dissociate the hybrid; determining a Tm value which is a temperature at which the hybrid dissociates based on the change in the fluorescent signal; and determining whether or not polymorphism of the CYP3A gene is present in the single-stranded nucleic acid in the sample based on the Tm value. In additional embodiments, further comprising amplifying the nucleic acid before or at the same time as contacting the probe with a single-stranded nucleic acid in a sample and hybridizing the probe and the single-stranded nucleic acid to obtain a hybrid.

The present invention according to some embodiments further includes a method of evaluating a drug efficacy or tolerance may comprise: detecting a polymorphism in the CYP3A gene by the method described herein; and evaluating tolerance to the drug or the efficacy of the drug based on the presence or absence of the polymorphism.

The present invention according to some embodiments also includes a reagent kit for detecting polymorphism in the CYP3A gene may comprise the probe described herein. In some embodiments, the reagent kit described herein further comprising a primer for amplifying a region including a sequence that the probe hybridizes. In some embodiments, the primer is selected from the group consisting of oligonucleotides P6, P6', P7, P7', P8, P8', P9, P9', P10, P10', wherein P6 is an oligonucleotide having a sequence having at least 80% identity to the 322nd to the 344th bases of SEQ ID NO: 1 and having a length of from 23 bases to 50 bases;

P6' is an oligonucleotide having a sequence being hybridized under stringent conditions to a complementary strand of the 322nd to the 344th bases of SEQ ID NO: 1 and having a length of from 23 bases to 50 bases;

P7 is an oligonucleotide having a sequence having at least 80% identity to a complementary strand of the 446th to the 463rd bases of SEQ ID NO: 1 and having a length of from 18 bases to 50 bases;

P7' is an oligonucleotide having a sequence being hybridized under stringent conditions to a base sequence including the 446th to the 463rd bases of SEQ ID NO: 1 and having a length of from 18 bases to 50 bases;

P8 is an oligonucleotide having a sequence having at least 80% identity to the 118th to the 137th bases of SEQ ID NO: 2 and having a length of from 20 bases to 50 bases;

P8' is an oligonucleotide having a sequence being hybridized under stringent conditions to a complementary strand of the 118th to the 137th bases of SEQ ID NO: 2 and having a length of from 20 bases to 50 bases;

P9 is an oligonucleotide having a sequence having at least 80% identity to the 22nd to the 49th bases of SEQ ID NO: 2 and having a length of from 28 bases to 50 bases;

P9' is an oligonucleotide having a sequence being hybridized under stringent conditions to a complementary strand of the 22nd to the 49th bases of SEQ ID NO: 2 and having a length of from 28 bases to 50 bases;

P10 is an oligonucleotide having a sequence having at least 80% identity to a complementary strand of the 292nd to the 312th bases of SEQ ID NO: 2 and having a length of from 21 bases to 50 bases; and P10' is an oligonucleotide having a sequence being hybridized under stringent conditions to the 292nd to the 312th bases of SEQ ID NO: 2 and having a length of from 21 bases to 50 bases.

According to the the present disclosures, a probe for detecting polymorphism that enables a simple detection of polymorphism in the CYP3A gene with high sensitivity and a method of detecting polymorphism using the probe can be provided. Further, the present invention can provide a method of evaluating a drug efficacy using the method of detecting polymorphism. Furthermore, the present invention can provide a reagent kit for detecting polymorphism using the probe for detecting polymorphism. The present invention can be applied to the detection of polymorphism in the CYP3A gene in a wide range of fields such as biochemistry and the like besides medical fields.

DETAILED DESCRIPTION OF THE INVENTION

Figure 1A:
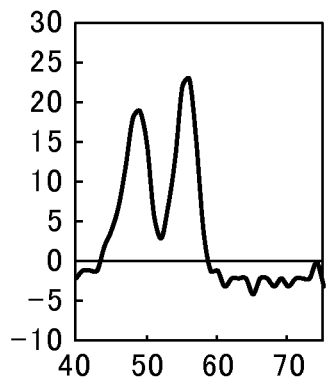
FIGS. 1A and 1B show melting curves of a sample according to Example 1 of the present invention.

The probe for detecting polymorphism in the CYP3A gene according to the present invention (hereinafter, this may simply be referred to as a "polymorphism detection probe") is a probe which detects polymorphism in the CYP3A gene and includes one fluorescently labeled oligonucleotide selected from the group consisting of P1, P1', P2, P2', P3, P3', P4, P4', P5, and P5' as described herein.

The method of detecting polymorphism in the CYP3A gene according to the present invention is a method including detecting polymorphism in the CYP3A gene using at least one of the probes which detect polymorphism in the CYP3A gene. The method of evaluating a drug efficacy or tolerance according to the present invention is a method including detecting polymorphism in the CYP3A gene by the method of detecting polymorphism in the CYP3A gene and evaluating tolerance to the drug or the efficacy of the drug based on the presence or absence of detected polymorphism. The reagent kit for detecting polymorphism according to the present invention is a reagent kit including the probe which detects polymorphism in the CYP3A gene.

The "CYP3A gene" in the present invention has already been known. The base sequence of the CYP3A5 gene refers to the sequence from 99245813 to 99277621 of NCBI Accession No. NC000007.13. SEQ ID NO: 1 that shows a partial sequence of the CYP3A5 gene is the sequence from 6683 to 7483 of NCBI dbSNP Accession No. NG007938. The base sequence of the CYP3A4 gene refers to the sequence from 99354583 to 99381811 of NCBI Accession No. NC000007.13. SEQ ID NO: 2 that shows a partial sequence of the CYP3A4 gene is the sequence from 15519 to 15928 of NCBI dbSNP Accession No. NG008421, and SEQ ID NO: 3 that shows a partial sequence of the CYP3A4 gene is the sequence from 24616172 to 24616872 of NCBI dbSNP Accession No. NT007933.14. In the base sequences of SEQ ID NOs: 1 to 3, r indicates a or g; s indicates c or g; w indicates a, t, or u; and v indicates g, a, or c.

In the CYP3A5 gene, the base (r) corresponding to the 401st base of the sequence indicated in SEQ ID NO: 1 is A (adenine) in relation to a wild type, and the base (r) is mutated to G (guanine) in relation to a mutant type. Hereinafter, the polymorphism in the CYP3A5 gene of SEQ ID NO: 1 is referred to as the "CYP3A5*3 polymorphism". In the CYP3A4 gene, the base(s) corresponding to the 201st base of the sequence indicated in SEQ ID NO: 2 is C (cytosine) in relation to a wild type, and the base(s) is mutated to G (guanine) in relation to a mutant type. Hereinafter, the polymorphism in the CYP3A4 gene of SEQ ID NO: 2 is referred to as the "CYP3A4*16 polymorphism".

In the CYP3A4 gene, the base (r) corresponding to the 501st base of the sequence indicated in SEQ ID NO: 3 is A (adenine) in relation to a wild type, and the base (r) is mutated to G (guanine) in relation to a mutant type. Hereinafter, the polymorphism in the CYP3A4 gene of SEQ ID NO: 3 is referred to as the "CYP3A4*1B polymorphism".

In the CYP3A gene, if at least one of the aforementioned three polymorphisms is a mutant type, for example, it can be determined that there is a possibility of decreasing metabolism of a drug, such as the immunosuppressant (e.g. tacrolimus). Accordingly, in one aspect of the present invention, a drug efficacy or tolerance may be evaluated or predicted by detecting polymorphism in the CYP3A gene by the method described herein, and evaluating tolerance to the drug or the efficacy of the drug based on the presence or absence of detected polymorphism.

Similarly, in another aspect of the present invention, the drugs whose efficacy or tolerance may be evaluated or predicted by methods described herein include, but do not limit to, (1) drugs that bind to specific sites on the GABAA gamma-amino-butyric acid receptor (e.g. alprazolam, estazolam, eszopiclone, midazolam); (2) drugs that stabilize the inactivated state of sodium channels (e.g. carbamazepine); (3) D2 partial agonist (e.g. aripiprazole); (4) serotonin 5-HT1A receptor partial agonist (e.g. buspirone); (5) selective serotonin reuptake inhibitor (e.g. citalopram, fluoxetine); (6) serotonin-norepinephrine reuptake inhibitor (e.g. amitriptyline); (7) drugs that block D2 receptors (e.g. haloperidol); (8) antagonist at the 5-HT2A receptors (e.g. nefazodone); (9) drugs that block postsynaptic receptors including, but not limited to, D1, D2, D3, D4 receptor antagonists, 5-HT1A, 5-HT2A, 5-HT2C, and 5-HT7 receptor antagonists, mACh receptor antagonist (e.g. pimozide, quentiapine); (10) steroids (e.g. fluticasone, salmeterol, zieuton; (11) antibiotics, antifungals, immunosuppressant (e.g. macrolides, not azithromycin, tacrolimus, itraconazole, ketoconazole, telithromycin; (12) anticonvulsants (e.g. carbamazepine, ethosuximide, felbamate, tiagabine, zonisamide); (13) antihistamines (e.f. desoloratadine, fexofenadine, loratadine); (14) drug of abuse/treatment (e.g. buprenorphine, cocaine, fentanyl, ketamine, methadone, oxycodone, phencyclidine); (15) calcium channel blockers (e.g. cortisols, desogestrel (p), ethynyl estradiol, progestins, progesterone, vincristine); (16) HIV inhibitor (e.g. ritonavir, saquinavir); (17) other drugs including, but not limited to, risperidone, sertraline, trazodone, triazolam, zaleplon, zolpidem, aprepitant, cinacalcet, esomeprazole, granisetron, nateglinide, omeprazole, pioglitazone, quinidine, sildenafil, statins, atorvastatin, lovastatin, simvastatin, and tolterodine.

In the present invention, with respect to the respective sequences of a sample nucleic acid in a sample to be detected, a polymorphism detection probe, and a primer, the matters described based on the complementary relationship therebetween are applied to the sequences complementary to the respective sequences unless otherwise noted. When the matters of the present invention are applied to the sequences complementary to the respective sequences, sequences recognized, detected, or bound by the complementary sequences shall be read as the corresponding sequences complementary to the sequences described in the specification within the scope of the common technical knowledge for those skilled in the art.

In the present invention, the "Tm value" is a temperature (dissociation temperature or melting temperature: Tm) at which double-stranded nucleic acid dissociates, and generally is defined as a temperature at which the absorbance at 260 nm reaches 50% of the total increase in absorbance. That is, when a solution containing double-stranded nucleic acid, for example double-stranded DNA, is heated, the absorbance at 260 nm increases. The increase results from the breakage of hydrogen bonds between the strands in the double-stranded DNA resulting from the heating and the dissociation into single-stranded DNA (DNA melting). When all double-stranded DNA dissociates to form single-stranded DNA, the absorbance exhibits approximately 1.5 times increase of the absorbance when commencing heating (absorbance when only double-stranded DNA is present). In this manner, completion of melting can be determined. The Tm value is set based on this phenomenon. The Tm value in the present invention is a temperature at the time when the absorbance reaches 50% of the total amount of increase in absorbance, unless otherwise noted.

In the specification, the "process" does not only refer to an independent process but also includes, for example, a case in which it cannot be clearly distinguished from other processes as long as the desired action of the present process is achieved. Further, in the present specification, a numerical value range expressed with "to" refers to a range including numerical values before and after "to" as a minimum value and a maximum value. Further, in the present invention, the amount of each component in composition refers to, in the case where plural materials corresponding to the component are present in the composition, the total amount of the plural materials present in the composition, unless otherwise noted. In the present invention, with respect to a sequence of oligonucleotide, the expression, "the 1st to the 3rd positions from the 3' end", is premised on that the 3' end of an oligonucleotide strand is counted as the 1st.

Hereinafter, the present invention will be described in more detail.

<CYP3A Gene Polymorphism Detection Probe>

The CYP3A gene polymorphism detection probe according to the present invention is a probe which detects polymorphism in the CYP3A gene and includes one labeled oligonucleotide selected from the group consisting of P1, P1', P2, P2', P3, P3', P4, P4', P5, and P5'.

In the CYP3A5 gene, the base (r) corresponding to the 401st base of the sequence indicated in SEQ ID NO: 1 is A (adenine) in relation to a wild type, and the base (r) is mutated to G (guanine) in relation to a mutant type. Hereinafter, the polymorphism in the CYP3A5 gene of SEQ ID NO: 1 is referred to as the "CYP3A5*3 polymorphism". Further, hereinafter, the probe for detecting this polymorphism is also referred to as the CYP3A5*3 probe.

In the present invention, one labeled oligonucleotide selected from the group consisting of P1 and P1' (hereinafter, this is also referred to as the "labeled oligonucleotide P1 or P1'") is a probe capable of detecting polymorphism in the 401st base of the base sequence indicated in SEQ ID NO: 1. In some embodiments, the labeled oligonucleotides described herein may be fluorescently labeled.

Specifically, the labeled oligonucleotide P1 of the present invention has a sequence including the 401st to the 411th bases of the sequence indicated in SEQ ID NO: 1. In the labeled oligonucleotide P1, for example, the base (r) corresponding to the 401st base of the base sequence indicated in SEQ ID NO: 1 may be A or G. As referred to herein, reference to "a base sequence having the same bases as SEQ ID NO." refers to a portion of said SEQ ID NO.'s sequence which appears in said probe subject to the modification(s) discussed herein.

(P1) labeled oligonucleotide having a sequence including the 401st to the 411th bases of the sequence indicated in SEQ ID NO: 1 and having a length of from 11 bases to 50 bases, the sequence having at least 80% identity with respect to a base sequence having the same bases as SEQ ID NO: 1 with the exception that the base corresponding to the 411th base in SEQ ID NO: 1 is cytosine, and, in some embodiments, the base corresponding to the 411th base of the base sequence indicated in SEQ ID NO: 1 being labeled with a fluorescent dye The labeled oligonucleotide P1 of the present invention has a sequence having identity with respect to a base sequence having the same bases as SEQ ID NO: 1 with the exception that the base corresponding to the 411th base in SEQ ID NO: 1 is C (cytosine). Specifically, the labeled oligonucleotide P1 of the present invention shows at least 80% identity with respect to a base sequence having the same bases as SEQ ID NO: 1 with the exception that the base corresponding to the 411th base in SEQ ID NO: 1 is C (cytosine). Further, from the viewpoint of detection sensitivity, for example, the labeled oligonucleotide P1 of the present invention may show at least 85% identity, at least 90% identity, at least 95% identity, at least 96% identity, at least 97% identity, at least 98% identity, or at least 99% identity. Further, in some embodiments, the labeled oligonucleotide P1 has a sequence having identity with respect to a base sequence having the same bases as SEQ ID NO: 1 with the exception that the base corresponding to the 411th base in SEQ ID NO: 1 is C (cytosine) and the base corresponding to the 401st base in SEQ ID NO: 1 is r (A or G).

For example, in the case where the labeled oligonucleotide P1 has a sequence in which the base corresponding to the 401st base in SEQ ID NO: 1 is mutant type G, for example, the following can be said. When the labeled oligonucleotide P1 of the present invention is compared with a base sequence having the same bases as SEQ ID NO: 1 with the exception that the base corresponding to the 411th base in SEQ ID NO: 1 is C (cytosine), in the case where the identity therebetween is less than 80%, the detection sensitivity to a sample nucleic acid containing the mutant type CYP3A5 gene decreases.

The labeled oligonucleotide P1 according to the present invention may be the labeled oligonucleotide that recognizes polymorphism of the 401st base in SEQ ID NO: 1, for example. The labeled oligonucleotide has, in addition to a specific base sequence, a function of recognizing polymorphism of the 401st base in SEQ ID NO: 1. Therefore, for example, in the case where the labeled oligonucleotide has a sequence in which the base corresponding to the 401st base in SEQ ID NO: 1 is mutant type G, the detection sensitivity to a sample nucleic acid containing the mutant type CYP3A5 gene tends to increase.

The labeled oligonucleotide P1' in the present invention has a sequence being hybridized under stringent conditions with respect to a complementary strand of a base sequence having the same bases as SEQ ID NO: 1 with the exception that the base corresponding to the 411th base in SEQ ID NO: 1 is C (cytosine). In the labeled oligonucleotide P1', for example, the base (r) corresponding to the 401st base of the base sequence indicated in SEQ ID NO: 1 may be A or G.

(P1') labeled oligonucleotide having a sequence including the 401st to the 411th bases of the sequence indicated in SEQ ID NO: 1 and having a length of from 11 bases to 50 bases, the sequence being hybridized under stringent conditions with respect to a complementary strand of a base sequence having the same bases as SEQ ID NO: 1 with the exception that the base corresponding to the 411th base in SEQ ID NO: 1 is cytosine, and, in some embodiments, the base corresponding to the 411th base of the sequence indicated in SEQ ID NO: 1 being labeled with a fluorescent dye.

The hybridization can be performed by a known method or based on a known method, for example, according to the method described in Molecular Cloning 3rd (J. Sambrook et al., Cold Spring Harbor Lab. Press, 2001). The entire subject matter of this document is incorporated herein by reference.

The stringent conditions refer to conditions where a specific hybrid is formed and a nonspecific hybrid is not formed. An example of a typical stringent condition include a condition where hybridization is performed in about 25 mmol/L to about 50 mmol/L potassium and about 1.0 mmol/L to about 5.0 mmol/L magnesium. An example of the condition of the present invention includes a condition where hybridization is performed in Tris-HCl (pH8.6), 25 mmol/L KCl, and 1.5 mmol/L $MgCl_2$. However, the present invention is not limited thereto. Besides this, stringent conditions are described in Molecular Cloning 3rd (J. Sambrook et al., Cold Spring Harbor Lab. Press, 2001). The entire subject matter of this document is incorporated herein by reference. Those skilled in the art can easily select such conditions by changing a hybridization reaction, a salt concentration of a hybridization reaction solution, or the like.

The labeled oligonucleotide P1' according to the present invention may be the labeled oligonucleotide that recognizes polymorphism of the 401st base in SEQ ID NO: 1, for example. The labeled oligonucleotide has, in addition to a specific base sequence, a function of recognizing polymorphism of the 401st base in SEQ ID NO: 1. Therefore, for example, in the case where the labeled oligonucleotide has a sequence in which the base corresponding to the 401st base in SEQ ID NO: 1 is mutant type G, the detection sensitivity to a sample nucleic acid containing the mutant type CYP3A gene tends to increase.

The labeled oligonucleotide P1 or P1' in the present invention includes labeled oligonucleotide obtained by inserting a base(s) into, deleting a base(s) from, or substituting a base(s) with a base(s) in the labeled oligonucleotide P1 or P1'. In the labeled oligonucleotide obtained by inserting a base(s) into, deleting a base(s) from, or substituting a base(s) with a base(s) in the labeled oligonucleotide P1 or P1', the position of the insertion, deletion, or substation is not particularly limited as long as an action comparable to the labeled oligonucleotide P1 or P1' can be achieved. The number of bases inserted, deleted, or substituted is, for example, one or more than one. The number of bases differs depending on the entire length of the labeled oligonucleotide, and is, for example, from 1 base to 10 bases or from 1 base to 5 bases.

Among them, the labeled oligonucleotide P1 or P1' in the present invention includes labeled oligonucleotide obtained by substituting a base(s) with a base(s) in the labeled oligonucleotide P1 or P1'. In the labeled oligonucleotide obtained by substituting a base(s) with a base(s) in the labeled oligonucleotide P1 or P1', the position of the substation is not particularly limited as long as an action comparable to the labeled oligonucleotide P1 or P1' can be achieved. From the viewpoint of detection sensitivity, for example, a base(s) positioned not at the 401st to the 411th bases of the sequence indicated in SEQ ID NO: 1 may be substituted. The number of bases substituted is, for example, one or more than one. The number of bases substituted differs depending on the entire length of the labeled oligonucleotide, and is, for example, from 1 base to 5 bases or from 1 base to 3 bases.

The length of the labeled oligonucleotide P1 or P1' of the present invention may be from 11 bases to 50 bases (mer). In the case where the length of the labeled oligonucleotide P1 or P1' is 10 bases or less or 51 bases or more, the detection sensitivity to polymorphism in the CYP3A gene decreases. Further, the length of the labeled oligonucleotide P1 or P1' can be, for example, from 15 bases to 30 bases, from 15 bases to 21 bases, or from 15 bases to 20 bases. For example, there is a tendency that the detection sensitivity is increased by designing the length as from 15 bases to 30 bases, for example. Furthermore, by changing the length of the labeled oligonucleotide P1 or P1', for example, a desirable value of the Tm value, which is a temperature at which the hybrid composed of the labeled oligonucleotide P1 or P1' and its complementary strand dissociates, can be obtained.

Examples of the base sequence of the labeled oligonucleotide P1 in the present invention are illustrated below. However, the present invention is not limited thereto.

```
                                        (SEQ ID NO: 37)
    5'-ttgtctttcartatctcttcc-3'

(3FL-CYP3A5*3-mt-F1-21)
                                        (SEQ ID NO: 4)
    5'-ttgtattcagtatctatcc-3'

(SEQ ID NO: 5)
    5'-ttgtctttcaatatctcttcc-3'
```

In the fluorescently labeled oligonucleotide P1 or P1' according to some embodiments of the present invention, the base corresponding to the 411th base of the sequence indicated in SEQ ID NO: 1 is labeled with a fluorescent dye.

In the fluorescently labeled oligonucleotide P1 or P1' according to some embodiments of the present invention, the 411th base labeled with a fluorescent dye can be at a position of any one of the 1st to the 3rd positions from the 3' end or at the 3' end. Thereby, for example, the detection sensitivity to polymorphism further increases and the fluorescently labeled oligonucleotide P1 or P1' can be obtained with high productivity.

In the present invention, one labeled oligonucleotide selected from the group consisting of P2, P2', P3, P3', P4, and P4' (hereinafter, this is also referred to as the "labeled oligonucleotide P2, P2', P3, P3', P4, or P4'") is a probe capable of detecting polymorphism in the 201st base of the base sequence indicated in SEQ ID NO: 2.

In the CYP3A4 gene, the base(s) corresponding to the 201st base of the sequence indicated in SEQ ID NO: 2 is C (cytosine) in relation to a wild type, and the base(s) is mutated to G (guanine) in relation to a mutant type. Hereinafter, the polymorphism in the CYP3A4 gene of SEQ ID NO: 2 is referred to as the "CYP3A4*16 polymorphism". Hereinafter, the probe for detecting this polymorphism is also referred to as the CYP3A4*16 probe.

Specifically, the labeled oligonucleotide P2 of the present invention has a sequence including the 201st to the 205th bases of the sequence indicated in SEQ ID NO: 2. In the labeled oligonucleotide P2, for example, the base(s) corresponding to the 201st base of the base sequence indicated in SEQ ID NO: 2 may be C or G.

(P2) labeled oligonucleotide having a sequence including the 201st to the 205th bases of the sequence indicated in SEQ ID NO: 2 and having a length of from 5 bases to 50 bases, the sequence having at least 80% identity with respect to a base sequence having the same bases as SEQ ID NO: 2 with the exception that the base corresponding to the 205th base in SEQ ID NO: 2 is cytosine, and, in some embodiments, the base corresponding to the 205th base of the sequence indicated in SEQ ID NO: 2 being labeled with a fluorescent dye.

The labeled oligonucleotide P2 of the present invention may have a sequence having identity with respect to a base sequence having the same bases as SEQ ID NO: 2 with the exception that the base corresponding to the 205th base in SEQ ID NO: 2 is C (cytosine). Specifically, the labeled oligonucleotide P2 of the present invention shows at least 80% identity with respect to a base sequence having the same bases as SEQ ID NO: 2 with the exception that the base corresponding to the 205th base in SEQ ID NO: 2 is C (cytosine). Further, from the viewpoint of detection sensitivity, for example, the labeled oligonucleotide P2 of the present invention may show at least 85% identity, at least 90% identity, at least 95% identity, at least 96% identity, at least 97% identity, at least 98% identity, or at least 99% identity. Further, in some embodiments, the labeled oligonucleotide P2 has a sequence having identity with respect to a base sequence having the same bases as SEQ ID NO: 2 with the exception that the base corresponding to the 205th base in SEQ ID NO: 2 is C (cytosine) and the base corresponding to the 201st base in SEQ ID NO: 2 is s (C or G).

For example, in the case where the labeled oligonucleotide P2 has a sequence in which the base corresponding to the 201st base in SEQ ID NO: 2 is mutant type G, for example, the following can be said. When the labeled oligonucleotide P2 of the present invention is compared with a base sequence having the same bases as SEQ ID NO: 2 with the exception that the base corresponding to the 205th base in SEQ ID NO: 2 is C (cytosine), in the case where the identity therebetween is less than 80%, the detection sensitivity to a sample nucleic acid containing the mutant type CYP3A4 gene decreases.

The labeled oligonucleotide P2 according to the present invention may be the labeled oligonucleotide that recognizes polymorphism of the 201st base in SEQ ID NO: 2, for example. The labeled oligonucleotide has, in addition to a specific base sequence, a function of recognizing polymorphism of the 201st base in SEQ ID NO: 2. Therefore, for example, in the case where the labeled oligonucleotide has a sequence in which the base corresponding to the 201st base in SEQ ID NO: 2 is mutant type G, the detection sensitivity to a sample nucleic acid containing the mutant type CYP3A4 gene tends to increase.

The labeled oligonucleotide P2' in the present invention has a sequence being hybridized under stringent conditions with respect to a complementary strand of a base sequence having the same bases as SEQ ID NO: 2 with the exception that the base corresponding to the 205th base in SEQ ID NO: 2 is C (cytosine). In the labeled oligonucleotide P2', for example, the base(s) corresponding to the 201st base of the base sequence indicated in SEQ ID NO: 2 may be C or G. The hybridization and the stringent conditions are the same as those described herein.

(P2') labeled oligonucleotide having a sequence including the 201st to the 205th bases of the sequence indicated in SEQ ID NO: 2 and having a length of from 5 bases to 50 bases, the sequence being hybridized under stringent conditions with respect to a complementary strand of a base sequence having the same bases as SEQ ID NO: 2 with the exception that the base corresponding to the 205th base in SEQ ID NO: 2 is cytosine, and, in some embodiments, the base corresponding to the 205th base of the sequence indicated in SEQ ID NO: 2 being labeled with a fluorescent dye.

The labeled oligonucleotide P2' according to the present invention may be the labeled oligonucleotide that recognizes polymorphism of the 201st base in SEQ ID NO: 2, for example. The labeled oligonucleotide has, in addition to a specific base sequence, a function of recognizing polymorphism of the 201st base in SEQ ID NO: 2. Therefore, for example, in the case where the labeled oligonucleotide has a sequence in which the base corresponding to the 201st base in SEQ ID NO: 2 is mutant type G, the detection sensitivity to a sample nucleic acid containing the mutant type CYP3A4 gene tends to increase.

The labeled oligonucleotide P2 or P2' in the present invention includes labeled oligonucleotide obtained by inserting a base(s) into, deleting a base(s) from, or substituting a base(s) with a base(s) in the labeled oligonucleotide P2 or P2'. In the labeled oligonucleotide obtained by inserting a base(s) into, deleting a base(s) from, or substituting a base(s) with a base(s) in the labeled oligonucleotide P2 or P2', the position of the insertion, deletion, or substation is not particularly limited as long as an action comparable to the labeled oligonucleotide P2 or P2' can be achieved. The number of bases inserted, deleted, or substituted is, for example, one or more than one. The number of bases differs depending on the entire length of the labeled oligonucleotide, and is, for example, from 1 base to 10 bases or from 1 base to 5 bases.

Among them, the labeled oligonucleotide P2 or P2' in the present invention includes labeled oligonucleotide obtained by substituting a base(s) with a base(s) in the labeled oligonucleotide P2 or P2'. In the labeled oligonucleotide obtained by substituting a base(s) with a base(s) in the labeled oligonucleotide P2 or P2', the position of the substation is not particularly limited as long as an action comparable to the labeled oligonucleotide P2 or P2' can be achieved. From the viewpoint of detection sensitivity, for example, a base(s) positioned not at the 201st to the 205th bases of the sequence indicated in SEQ ID NO: 2 may be substituted. The number of bases substituted is, for example, one or more than one. The number of bases substituted differs depending on the entire length of the labeled oligonucleotide, and is, for example, from 1 base to 5 bases or from 1 base to 3 bases.

The length of the labeled oligonucleotide P2 or P2' of the present invention may be from 5 bases to 50 bases (mer). In the case where the length of the labeled oligonucleotide P2 or P2' is 4, 5, 6, 7, 8, 9, or 10 bases or less or 51 bases or more, the detection sensitivity to polymorphism in the CYP3A gene decreases. Further, the length of the labeled oligonucleotide P2 or P2' can be, for example, from 10 bases to 30 bases or from 10 bases to 20 bases. For example, there is a tendency that the detection sensitivity is increased by designing the length as from 10 bases to 30 bases, for example. Furthermore, by changing the length of the labeled oligonucleotide P2 or P2', for example, a desirable value of the Tm value, which is a temperature at which the hybrid composed of the labeled oligonucleotide P2 or P2' and its complementary strand dissociates, can be obtained.

Examples of the base sequence of the labeled oligonucleotide P2 in the present invention are illustrated below. However, the present invention is not limited thereto.

```
                                              (SEQ ID NO: 38)
        5'-gatgtgatcagtagc-3'

(3T-CYP3A4*16-MF1)
                                              (SEQ ID NO: 6)
        5'-gatgtgatcagtagc-3'

(SEQ ID NO: 7)
        5'-gatgtgatcactagc-3'
```

In the fluorescently labeled oligonucleotide P2 or P2' according to some embodiments of the present invention, the base corresponding to the 205th base of the sequence indicated in SEQ ID NO: 2 is labeled with a fluorescent dye.

In the fluorescently labeled oligonucleotide P2 or P2' according to some embodiments of the present invention, the 205th base labeled with a fluorescent dye can be at a position of any one of the 1st to the 3rd positions from the 3' end or at the 3' end. Thereby, for example, the detection sensitivity to polymorphism further increases and the fluorescently labeled oligonucleotide P2 or P2' can be obtained with high productivity.

In the present invention, in the labeled oligonucleotides P3 and P3', for example, the base(s) complementary to the 201st base of the base sequence indicated in SEQ ID NO: 2 may be G or C.

Specifically, the labeled oligonucleotide P3 of the present invention has a sequence complementary to a sequence including the 190th to the 201st bases of the sequence indicated in SEQ ID NO: 2. In the labeled oligonucleotide P3, for example, the base(s) complementary to the 201st base of the base sequence indicated in SEQ ID NO: 2 may be C or G.

(P3) labeled oligonucleotide having a sequence complementary to a sequence including the 190th to the 201st bases of the sequence indicated in SEQ ID NO: 2 and having a length of from 12 bases to 50 bases, the sequence having at least 80% identity with respect to a base sequence having the same bases as a complementary strand of SEQ ID NO: 2 with the exception that the base complementary to the 190th base in SEQ ID NO: 2 is cytosine, and, in some embodiments, the base complementary to the 190th base of the sequence indicated in SEQ ID NO: 2 being labeled with a fluorescent dye The labeled oligonucleotide P3 of the present invention has a sequence having identity with respect to a base sequence having the same bases as a complementary strand of SEQ ID NO: 2 with the exception that the base complementary to the 190th base in SEQ ID NO: 2 is C (cytosine). Specifically, the labeled oligonucleotide P3 of the present invention shows at least 80% identity with respect to a base sequence having the same bases as a complementary strand of SEQ ID NO: 2 with the exception that the base complementary to the 190th base in SEQ ID NO: 2 is C (cytosine). Further, from the viewpoint of detection sensitivity, for example, the labeled oligonucleotide P3 of the present invention may show at least 85% identity, at least 90% identity, at least 95% identity, at least 96% identity, at least 97% identity, at least 98% identity, or at least 99% identity. Further, in some embodiments, the labeled oligonucleotide P3 has a sequence having identity with respect to a base sequence having the same bases as a complementary strand of SEQ ID NO: 2 with the exception that the base complementary to the 190th base in SEQ ID NO: 2 is C (cytosine) and the base complementary to the 201st base in SEQ ID NO: 2 is s (C or G).

For example, in the case where the labeled oligonucleotide P3 has a sequence in which the base complementary to the 201st base in SEQ ID NO: 2 is mutant type C, for example, the following can be said. When the labeled oligonucleotide P3 of the present invention is compared with a base sequence having the same bases as a complementary strand of SEQ ID NO: 2 with the exception that the base complementary to the 190th base in SEQ ID NO: 2 is C (cytosine), in the case where the identity therebetween is less than 80%, the detection sensitivity to a sample nucleic acid containing the mutant type CYP3A4 gene decreases.

The labeled oligonucleotide P3 according to the present invention may be the labeled oligonucleotide that recognizes polymorphism of the 201st base in SEQ ID NO: 2, for example. The labeled oligonucleotide has, in addition to a specific base sequence, a function of recognizing polymorphism of the 201st base in SEQ ID NO: 2. Therefore, for example, in the case where the labeled oligonucleotide has a sequence in which the base complementary to the 201st base in SEQ ID NO: 2 is mutant type C, the detection sensitivity to a sample nucleic acid containing the mutant type CYP3A4 gene tends to increase.

The labeled oligonucleotide P3' in the present invention has a sequence being hybridized under stringent conditions with respect to a base sequence having the same bases as SEQ ID NO: 2 with the exception that the base complementary to the 190th base in SEQ ID NO: 2 is C (cytosine). In the labeled oligonucleotide P3', for example, the base(s) complementary to the 201st base of the base sequence indicated in SEQ ID NO: 2 may be C or G. The hybridization and the stringent conditions are the same as those described herein.

(P3') labeled oligonucleotide having a sequence complementary to a sequence including the 190th to the 201st bases of the sequence indicated in SEQ ID NO: 2 and having a length of from 12 bases to 50 bases, the sequence being hybridized under stringent conditions with respect to a base sequence having the same bases as SEQ ID NO: 2 with the exception that the base complementary to the 190th base in SEQ ID NO: 2 is cytosine, and, in some embodiments, the base complementary to the 190th base of the sequence indicated in SEQ ID NO: 2 being labeled with a fluorescent dye The labeled oligonucleotide P3' according to the present invention may be the labeled oligonucleotide that recognizes polymorphism of the 201st base in SEQ ID NO: 2, for example. The labeled oligonucleotide has, in addition to a specific base sequence, a function of recognizing polymorphism of the 201st base in SEQ ID NO: 2. Therefore, for example, in the case where the labeled oligonucleotide has a sequence in which the base complementary to the 201st base in SEQ ID NO: 2 is mutant type C, the detection sensitivity to a sample nucleic acid containing the mutant type CYP3A4 gene tends to increase.

The labeled oligonucleotide P3 or P3' in the present invention includes labeled oligonucleotide obtained by inserting a base(s) into, deleting a base(s) from, or substituting a base(s) with a base(s) in the labeled oligonucleotide P3 or P3'. In the labeled oligonucleotide obtained by inserting a base(s) into, deleting a base(s) from, or substituting a base(s) with a base(s) in the labeled oligonucleotide P3 or P3', the position of the insertion, deletion, or substation is not particularly limited as long as an action comparable to the labeled oligonucleotide P3 or P3' can be achieved. The number of bases inserted, deleted, or substituted is, for example, one or more than one. The number of bases differs depending on the entire length of the labeled oligonucleotide, and is, for example, from 1 base to 10 bases or from 1 base to 5 bases.

Among them, the labeled oligonucleotide P3 or P3' in the present invention includes labeled oligonucleotide obtained by substituting a base(s) with a base(s) in the labeled oligonucleotide P3 or P3'. In the labeled oligonucleotide obtained by substituting a base(s) with a base(s) in the labeled oligonucleotide P3 or P3', the position of the substation is not particularly limited as long as an action comparable to the labeled oligonucleotide P3 or P3' can be achieved. From the viewpoint of detection sensitivity, for example, the base(s) complementary to a base(s) positioned not at the 190th to the 201st bases of the sequence indicated in SEQ ID NO: 3 may be substituted. The number of bases substituted is, for example, one or more than one. The number of bases substituted differs depending on the entire length of the labeled oligonucleotide, and is, for example, from 1 base to 5 bases or from 1 base to 3 bases.

The length of the labeled oligonucleotide P3 or P3' of the present invention may be from 12 bases to 50 bases (mer). In the case where the length of the labeled oligonucleotide P3 or P3' is 11 bases or less or 51 bases or more, the detection sensitivity to polymorphism in the CYP3A gene decreases. Further, the length of the labeled oligonucleotide P3 or P3' can be, for example, from 12 bases to 40 bases or from 15 bases to 30 bases. For example, there is a tendency that the detection sensitivity is increased by designing the length as from 12 bases to 40 bases, for example. Furthermore, by changing the length of the labeled oligonucleotide P3 or P3', for example, a desirable Tm value, which is a temperature at which the hybrid composed of the labeled oligonucleotide P3 or P3' and its complementary strand dissociates, can be obtained.

Examples of the base sequence of the labeled oligonucleotide P3 in the present invention are illustrated below. However, the present invention is not limited thereto.

```
                                    (SEQ ID NO: 39)
       5'-tgtgctastgatcacatcc-3'

(3T-CYP3A4*16-MR1)
                                    (SEQ ID NO: 8)
       5'-tgtgctactgatcacatcc-3'

(SEQ ID NO: 40)
       5'-tgtgctagtgatcacatcc-3'
```

In the fluorescently labeled oligonucleotide P3 or P3' according to some embodiments of the present invention, the base complementary to the 190th base of the sequence indicated in SEQ ID NO: 2 is labeled with a fluorescent dye.

In the fluorescently labeled oligonucleotide P3 or P3' according to some embodiments of the present invention, the base complementary to the 190th base labeled with a fluorescent dye can be at a position of any one of the 1st to the 3rd positions from the 3' end or at the 3' end. Thereby, for example, the detection sensitivity to polymorphism further increases and the fluorescently labeled oligonucleotide P3 or P3' can be obtained with high productivity.

In the present invention, in the labeled oligonucleotides P4 and P4', for example, the base(s) complementary to the 201st base of the base sequence indicated in SEQ ID NO: 2 may be G or C.

Specifically, the labeled oligonucleotide P4 of the present invention has a sequence complementary to a sequence including the 186th to the 201st bases of the sequence indicated in SEQ ID NO: 2. In the labeled oligonucleotide P4, for example, the base(s) complementary to the 201st base of the base sequence indicated in SEQ ID NO: 2 may be C or G.

(P4) labeled oligonucleotide having a sequence complementary to a sequence including the 186th to the 201st bases of the sequence indicated in SEQ ID NO: 2 and having a length of from 16 bases to 50 bases, the sequence having at least 80% identity with respect to a base sequence having the same bases as a complementary strand of SEQ ID NO: 2 with the exception that the base complementary to the 186th base in SEQ ID NO: 2 is cytosine, and, in some embodiments, the base complementary to the 186th base of the sequence indicated in SEQ ID NO: 2 being labeled with a fluorescent dye The labeled oligonucleotide P4 of the present invention has a sequence having identity with respect to a base sequence having the same bases as a complementary strand of SEQ ID NO: 2 with the exception that the base complementary to the 186th base in SEQ ID NO: 2 is C (cytosine). Specifically, the labeled oligonucleotide P4 of the present invention shows at least 80% identity with respect to a base sequence having the same bases as a complementary strand of SEQ ID NO: 2 with the exception that the base complementary to the 186th base in SEQ ID NO: 2 is C (cytosine). Further, from the viewpoint of detection sensitivity, for example, the labeled oligonucleotide P4 of the present invention may show at least 85% identity, at least 90% identity, at least 95% identity, at least 96% identity, at least 97% identity, at least 98% identity, or at least 99% identity. Further, in some embodiments, the labeled oligonucleotide P4 has a sequence having identity with respect to a base sequence having the same bases as a complementary strand of SEQ ID NO: 2 with the exception that the base complementary to the 205th base in SEQ ID NO: 2 is C (cytosine) and the base complementary to the 201st base in SEQ ID NO: 2 is s (C or G).

For example, in the case where the labeled oligonucleotide P4 has a sequence in which the base complementary to the 201st base in SEQ ID NO: 2 is mutant type C, for example, the following can be said. When the labeled oligonucleotide P4 of the present invention is compared with a base sequence having the same bases as a complementary strand of SEQ ID NO: 2 with the exception that the base complementary to the 186th base in SEQ ID NO: 2 is C (cytosine), in the case where the identity therebetween is less than 80%, the detection sensitivity to a sample nucleic acid containing the mutant type CYP3A4 gene decreases.

The labeled oligonucleotide P4 according to the present invention may be the labeled oligonucleotide that recognizes polymorphism of the 201st base in SEQ ID NO: 2, for example. The labeled oligonucleotide has, in addition to a specific base sequence, a function of recognizing polymorphism of the 201st base in SEQ ID NO: 2. Therefore, for example, in the case where the labeled oligonucleotide has a sequence in which the base complementary to the 201st base in SEQ ID NO: 2 is mutant type C, the detection sensitivity to a sample nucleic acid containing the mutant type CYP3A4 gene tends to increase.

The labeled oligonucleotide P4' in the present invention has a sequence being hybridized under stringent conditions with respect to a base sequence having the same bases as SEQ ID NO: 2 with the exception that the base complementary to the 186th base in SEQ ID NO: 2 is C (cytosine). In the labeled oligonucleotide P4', for example, the base(s) complementary to the 201st base of the base sequence indicated in SEQ ID NO: 2 may be C or G. The hybridization and the stringent conditions are the same as those described herein.

(P4') labeled oligonucleotide having a sequence complementary to a sequence including the 186th to the 201st bases of the sequence indicated in SEQ ID NO: 2 and having a length of from 16 bases to 50 bases, the sequence being hybridized under stringent conditions with respect to a base sequence having the same bases as SEQ ID NO: 2 with the exception that the base complementary to the 186th base in SEQ ID NO: 2 is cytosine, and, in some embodiments, the base complementary to the 186th base of the sequence indicated in SEQ ID NO: 2 being labeled with a fluorescent dye The labeled oligonucleotide P4' according to the present invention may be the labeled oligonucleotide that recognizes polymorphism of the 201st base in SEQ ID NO: 2, for example. The labeled oligonucleotide has, in addition to a specific base sequence, a function of recognizing polymorphism of the 201st base in SEQ ID NO: 2. Therefore, for example, in the case where the labeled oligonucleotide has a sequence in which the base complementary to the 201st base in SEQ ID NO: 2 is mutant type C, the detection sensitivity to a sample nucleic acid containing the mutant type CYP3A gene tends to increase.

The labeled oligonucleotide P4 or P4' in the present invention includes labeled oligonucleotide obtained by inserting a base(s) into, deleting a base(s) from, or substituting a base(s) with a base(s) in the labeled oligonucleotide P4 or P4'. In the labeled oligonucleotide obtained by inserting a base(s) into, deleting a base(s) from, or substituting a base(s) with a base(s) in the labeled oligonucleotide P4 or P4', the position of the insertion, deletion, or substation is not particularly limited as long as an action comparable to the labeled oligonucleotide P4 or P4' can be achieved. The number of bases inserted, deleted, or substituted is, for example, one or more than one. The number of bases differs depending on the entire length of the labeled oligonucleotide, and is, for example, from 1 base to 10 bases or from 1 base to 5 bases.

Among them, the labeled oligonucleotide P4 or P4' in the present invention includes labeled oligonucleotide obtained by substituting a base(s) with a base(s) in the labeled oligonucleotide P4 or P4'. In the labeled oligonucleotide obtained by substituting a base(s) with a base(s) in the labeled oligonucleotide P4 or P4', the position of the substation is not particularly limited as long as an action comparable to the labeled oligonucleotide P4 or P4' can be achieved. From the viewpoint of detection sensitivity, for example, the base(s) complementary to a base(s) positioned not at the 186th to the 201st bases of the sequence indicated in SEQ ID NO: 2 may be substituted. The number of bases substituted is, for example, one or more than one. The number of bases substituted differs depending on the entire length of the labeled oligonucleotide, and is, for example, from 1 base to 5 bases or from 1 base to 3 bases.

The length of the labeled oligonucleotide P4 or P4' of the present invention may be from 16 bases to 50 bases (mer). In the case where the length of the labeled oligonucleotide P4 or P4' is 15 bases or less or 51 bases or more, the detection sensitivity to polymorphism in the CYP3A gene decreases. Further, the length of the labeled oligonucleotide P4 or P4' can be, for example, from 16 bases to 40 bases or from 20 bases to 30 bases. For example, there is a tendency that the detection sensitivity is increased by designing the length as from 16 bases to 40 bases, for example. Furthermore, by changing the length of the labeled oligonucleotide P4 or P4', for example, a desirable Tm value, which is a temperature at which the hybrid composed of the labeled oligonucleotide P4 or P4' and its complementary strand dissociates, can be obtained.

Examples of the base sequence of the labeled oligonucleotide P4 in the present invention are illustrated below. However, the present invention is not limited thereto.

```
                                                    (SEQ ID NO: 41)
    5'-atgatgtgctastgatcacatccatgc-3'

(U0-3TMR4)
                                                    (SEQ ID NO: 10)
    5'-atgatgtgctactgatcacatccatgc-3'

(SEQ ID NO: 42)
    5'-atgatgtgctagtgatcacatccatgc-3'

(SEQ ID NO: 43)
    5'-gatgtgctastgatcacatccatgc-3'

(SEQ ID NO: 44)
    5'-gatgtgctactgatcacatccatgc-3'

(SEQ ID NO: 11)
    5'-gatgtgctagtgatcacatccatgc-3'
```

In the fluorescently labeled oligonucleotide P4 or P4' according to some embodiments of the present invention, the base complementary to the 186th base of the sequence indicated in SEQ ID NO: 2 is labeled with a fluorescent dye.

In the fluorescently labeled oligonucleotide P4 or P4' according to some embodiments of the present invention, the base complementary to the 186th base labeled with a fluorescent dye can be at a position of any one of the 1st to the 3rd positions from the 3' end or at the 3' end. Thereby, for example, the detection sensitivity to polymorphism further increases and the fluorescently labeled oligonucleotide P4 or P4' can be obtained with high productivity.

In the present invention, one labeled oligonucleotide selected from the group consisting of P5 and P5' (hereinafter, this is also referred to as the "labeled oligonucleotide P5 or P5'") is a probe capable of detecting polymorphism in the 501st base of the base sequence indicated in SEQ ID NO: 3.

(P5) labeled oligonucleotide having a sequence complementary to a sequence including the 496th to the 501st bases of the sequence indicated in SEQ ID NO: 3 and having a length of from 6 bases to 50 bases, the sequence having at least 80% identity with respect to a base sequence having the same bases as a complementary strand of SEQ ID NO: 3 with the exception that the base complementary to the 496th base in SEQ ID NO: 3 is cytosine, and, in some embodiments, the base complementary to the 496th base of the sequence indicated in SEQ ID NO: 3 being labeled with a fluorescent dye (P5') labeled oligonucleotide having a sequence complementary to a sequence including the 496th to the 501st bases of the sequence indicated in SEQ ID NO: 3 and having a length of from 6 bases to 50 bases, the sequence being hybridized under stringent conditions with respect to a base sequence having the same bases as SEQ ID NO: 3 with the exception that the base complementary to the 496th base in SEQ ID NO: 3 is cytosine, and the base complementary to the 496th base of the sequence indicated in SEQ ID NO: 3 being labeled with a fluorescent dye In the CYP3A4 gene, the base (r) corresponding to the 501st base of the sequence indicated in SEQ ID NO: 3 is A (adenine) in relation to a wild type, and the base (r) is mutated to G (guanine) in relation to a mutant type. Hereinafter, the polymorphism in the CYP3A4 gene of SEQ ID NO: 3 is referred to as the "CYP3A4*1B polymorphism". Hereinafter, the probe for detecting this polymorphism is also referred to as the CYP3A4*1B probe.

In the present invention, in the labeled oligonucleotides P5 and P5', for example, the base (y) complementary to the 501st base of the base sequence indicated in SEQ ID NO: 3 may be C or T.

Specifically, the labeled oligonucleotide P5 of the present invention has a sequence complementary to a sequence including the 496th to the 501st bases of the sequence indicated in SEQ ID NO: 3. In the labeled oligonucleotide P5, for example, the base (y) complementary to the 501st base of the base sequence indicated in SEQ ID NO: 3 may be C or T.

The labeled oligonucleotide P5 of the present invention has a sequence having identity with respect to a base sequence having the same bases as a complementary strand of SEQ ID NO: 3 with the exception that the base complementary to the 496th base in SEQ ID NO: 3 is C (cytosine). Specifically, the labeled oligonucleotide P5 of the present invention shows at least 80% identity with respect to a base sequence having the same bases as a complementary strand of SEQ ID NO: 3 with the exception that the base complementary to the 496th base in SEQ ID NO: 3 is C (cytosine). Further, from the viewpoint of detection sensitivity, for example, the labeled oligonucleotide P5 of the present invention may show at least 85% identity, at least 90% identity, at least 95% identity, at least 96% identity, at least 97% identity, at least 98% identity, or at least 99% identity. Further, in some embodiments, the labeled oligonucleotide P5 has a sequence having identity with respect to a base sequence having the same bases as a complementary strand of SEQ ID NO: 3 with the exception that the base complementary to the 496th base in SEQ ID NO: 3 is C (cytosine) and the base complementary to the 501st base in SEQ ID NO: 3 is y (C or T). In this case, for example, the identity is the same as that described herein.

For example, in the case where the labeled oligonucleotide P5 has a sequence in which the base complementary to the 501st base in SEQ ID NO: 3 is mutant type C, for example, the following can be said. When the labeled oligonucleotide P5 of the present invention is compared with a base sequence having the same bases as a complementary strand of SEQ ID NO: 5 with the exception that the base complementary to the 496th base in SEQ ID NO: 5 is C (cytosine), in the case where the identity therebetween is less than 80%, the detection sensitivity to a sample nucleic acid containing the mutant type CYP3A4 gene decreases.

The labeled oligonucleotide P5 according to the present invention may be the labeled oligonucleotide that recognizes polymorphism of the 501st base in SEQ ID NO: 3, for example. The labeled oligonucleotide has, in addition to a specific base sequence, a function of recognizing polymorphism of the 501st base in SEQ ID NO: 3. Therefore, for example, in the case where the labeled oligonucleotide has a sequence in which the base complementary to the 501st base in SEQ ID NO: 3 is mutant type C, the detection sensitivity to a sample nucleic acid containing the mutant type CYP3A4 gene tends to increase.

The labeled oligonucleotide 5' in the present invention has a sequence being hybridized under stringent conditions with respect to a base sequence having the same bases as SEQ ID NO: 3 with the exception that the base complementary to the 496th base in SEQ ID NO: 3 is C (cytosine). In the labeled oligonucleotide P5', for example, the base (y) complementary to the 501st base of the base sequence indicated in SEQ ID NO: 3 may be C or T. The hybridization and the stringent conditions are the same as those described herein.

The labeled oligonucleotide P5' according to the present invention may be the labeled oligonucleotide that recognizes polymorphism of the 501st base in SEQ ID NO: 3, for example. The labeled oligonucleotide has, in addition to a specific base sequence, a function of recognizing polymorphism of the 501st base in SEQ ID NO: 3. Therefore, for example, in the case where the labeled oligonucleotide has a sequence in which the base complementary to the 501st base in SEQ ID NO: 3 is mutant type C, the detection sensitivity to a sample nucleic acid containing the mutant type CYP3A4 gene tends to increase.

The labeled oligonucleotide P5 or P5' in the present invention includes labeled oligonucleotide obtained by inserting a base(s) into, deleting a base(s) from, or substituting a base(s) with a base(s) in the labeled oligonucleotide P5 or P5'. In the labeled oligonucleotide obtained by inserting a base(s) into, deleting a base(s) from, or substituting a base(s) with a base(s) in the labeled oligonucleotide P5 or P5', the position of the insertion, deletion, or substation is not particularly limited as long as an action comparable to the labeled oligonucleotide P5 or P5' can be achieved. The number of bases inserted, deleted, or substituted is, for example, one or more than one. The number of bases differs depending on the entire length of the labeled oligonucleotide, and is, for example, from 1 base to 10 bases or from 1 base to 5 bases.

Among them, the labeled oligonucleotide P5 or P5' in the present invention includes labeled oligonucleotide obtained by substituting a base(s) with a base(s) in the labeled oligonucleotide P5 or P5'. In the labeled oligonucleotide obtained by substituting a base(s) with a base(s) in the labeled oligonucleotide P5 or P5', the position of the substation is not particularly limited as long as an action comparable to the labeled oligonucleotide P5 or P5' can be achieved. From the viewpoint of detection sensitivity, for example, the base(s) complementary to a base(s) positioned not at the 496th to the 501st bases of the sequence indicated in SEQ ID NO: 3 may be substituted. The number of bases substituted is, for example, one or more than one. The number of bases substituted differs depending on the entire length of the labeled oligonucleotide, and is, for example, from 1 base to 5 bases or from 1 base to 3 bases.

The length of the labeled oligonucleotide P5 or P5' of the present invention may be from 6 bases to 50 bases (mer). In the case where the length of the labeled oligonucleotide P5 or P5' is 5, 6, 7, 8, 9, or 10 bases or less or 51 bases or more, the detection sensitivity to polymorphism in the CYP3A gene decreases. Further, the length of the labeled oligonucleotide P5 or P5' can be, for example, from 10 bases to 40 bases or from 20 bases to 30 bases. For example, there is a tendency that the detection sensitivity is increased by designing the length as from 10 bases to 40 bases, for example. Furthermore, by changing the length of the labeled oligonucleotide P5 or P5', for example, a desirable value of the Tm value, which is a temperature at which the hybrid composed of the labeled oligonucleotide P5 or P5' and its complementary strand dissociates, can be obtained.

Examples of the base sequence of the labeled oligonucleotide P5 in the present invention are illustrated below. However, the present invention is not limited thereto.

```
                                                  (SEQ ID NO: 45)
    5'-taaatcgccgctctcytgccc-3'

(3PB-CYP3A4*1B-R3)
                                                  (SEQ ID NO: 12)
    5'-taaatcgccgctctcctgccc-3'

(SEQ ID NO: 13)
    5'-taaatcgccgctctcttgccc-3'
```

In the fluorescently labeled oligonucleotide P5 or P5' according to some embodiments of the present invention, the base complementary to the 496th base of the sequence indicated in SEQ ID NO: 3 is labeled with a fluorescent dye.

In the fluorescently labeled oligonucleotide P5 or P5' according to some embodiments of the present invention, the base complementary to the 496th base labeled with a fluorescent dye can be at a position of any one of the 1st to the 3rd positions from the 3' end or at the 3' end. Thereby, for example, the detection sensitivity to polymorphism further increases and the fluorescently labeled oligonucleotide P5 or P5' can be obtained with high productivity.

With respect to the labeled oligonucleotides P1, P1', P2, P2', P3, P3', P4, P4', P5, and P5', the Tm value of the hybrid can be calculated using, for example, Meltcalc 99 free (meltcalc.com). Conditions for setting are not particularly limited and examples thereof. include Oligoconc [μM] 0.2 and Na eq. [mM] 50. Examples of the hybrid include: a hybrid composed of the labeled oligonucleotide in which the bases corresponding to the detection site are mutant type (mutant type labeled oligonucleotide) and a complementary sequence in which the detection site is mutant type or a complementary sequence in which the detection site is wild type; a hybrid composed of the labeled oligonucleotide in which the bases corresponding to the detection site are wild type (wild type labeled oligonucleotide) and a complementary sequence in which the detection site is mutant type or a complementary sequence in which the detection site is wild type. The difference between the Tm value of the hybrid composed of the mutant type labeled oligonucleotide and the mutant type complementary sequence and the Tm value of the hybrid composed of the mutant type labeled oligonucleotide and the wild type complementary sequence is, for example, at least 3° C., at least 4° C., or at least 5° C. and is, for example, not more than 30° C. Further, the difference between the Tm value of the hybrid composed of the wild type labeled oligonucleotide and the wild type complementary sequence and the Tm value of the hybrid composed of the wild type labeled oligonucleotide and the mutant type complementary sequence is, for example, at least 3° C., at least 4° C., at least 5° C., or at least 7° C. and is, for example, not more than 30° C.

The fluorescently labeled oligonucleotide described herein can be a fluorescently labeled oligonucleotide having the following characteristics. That is, the fluorescence intensity of the fluorescently labeled oligonucleotide when hybridized to its complementary strand is smaller (quenched) or larger than the fluorescence intensity when not hybridized to its complementary strand. Among them, the fluorescently labeled oligonucleotide of the present invention can be a fluorescently labeled oligonucleotide having the following characteristics. That is, the fluorescence intensity of the fluorescently labeled oligonucleotide when hybridized to its complementary strand is smaller than the fluorescence intensity when not hybridized to its complementary strand.

A probe utilizing such a fluorescence quenching phenomenon is generally referred to as a guanine quenching probe and is known as a so-called QProbe®. Among them, particularly preferable is an oligonucleotide designed such that the 3' end or the 5' end is cytosine (C) and labeled with a fluorescent dye such that an emission decreases as the base C at its end approaches guanine (G). The use of this type of probe enables simple confirmation of hybridization and dissociation in response to the change in the signal.

In addition to the detection method using a QProbe, a known detection method may be applied. This type of detection method includes, for example, a Taq-Man probe method, a hybridization probe method, a molecular beacon method, and a MGB probe method.

Examples of the fluorescent dye include, with no particular limitation, fluorescein, phosphor, rhodamine, and polymethine dye derivatives. Further, examples of the commercially available fluorescent dye include PACIFIC BLUE, BODIPY FL, FluorePrime, Fluoredite, FAM, Cy3 and Cy5, and TAMRA.

Conditions for detecting the fluorescently labeled oligonucleotide are not particularly limited and can be decided suitably according to the fluorescent dye used. For example, the detection wavelength for PACIFIC BLUE is 445 nm to 480 nm, the detection wavelength for TAMRA is 585 nm to 700 nm, and the detection wavelength for BODIPY FL is 520 nm to 555 nm.

The use of probes having the foregoing fluorescent dyes enables simple confirmation of hybridization and dissociation in response to the change in the respective fluorescence signals. The fluorescent dyes can be bonded to oligonucleotides by the usual method, for example, according to the method described in JP 2002-119291 A or the like.

Further, a phosphate group may be added to the 3' end of the fluorescently labeled oligonucleotide, for example. This is because the addition of a phosphate group to the 3' end of the fluorescently labeled oligonucleotide makes it possible to sufficiently suppress the elongation of the probe itself due to a gene amplification reaction. As will be described below, DNA (target DNA) to be detected whether or not a mutation is present can be prepared by a gene amplification method such as PCR or the like. At that time, the use of the fluorescently labeled oligonucleotide to which a phosphate group is added at the 3' end allows the oligonucleotide to coexist in a reaction solution for the amplification reaction. Furthermore the same effect can be obtained, for example, by adding the labeling substance (e.g. fluorescent dye) as described above to the 3' end of the probe.

Each of the labeled oligonucleotides described herein can be used as the CYP3A gene polymorphism detection probe which detects polymorphism in the CYP3A gene, particularly, CYP3A5*3, CYP3A4*16 and/or CYP3A4*1B. Further, the CYP3A gene polymorphism detection probe can be used as a probe for the melting curve analysis that will be described below.

For example, as the fluorescently labeled oligonucleotide of the present invention, a base labeled with a fluorescent dye based on the aforementioned condition can be used. Besides this, the fluorescently labeled oligonucleotide of the present invention can be produced by a known method known as an oligonucleotide synthesis method, for example, according to the method described in JP 2002-119291 A or the like.

<Primers>

In the method of detecting polymorphism in the CYP3A gene that will be described below, for example, in the case where a sequence containing the CYP3A gene polymorphism to be detected is amplified by an amplification method such as PCR or the like, a primer is used. The primer that can be used in the present invention is not particularly limited as long as a nucleic acid containing a polymorphism site of the CYP3A gene to be detected can be amplified. Examples of the nucleic acid include a nucleic acid including the base corresponding to the 401st base in SEQ ID NO: 1, a nucleic acid including the base corresponding to the 201st base in SEQ ID NO: 2, and a nucleic acid including the base corresponding to the 501st base in SEQ ID NO: 3.

The primer applied to the amplification method is not particularly limited as long as a region to which the polymorphism detection probe of the present invention can hybridize can be amplified. Those skilled art can design suitably from the base sequences indicated in SEQ ID NO: 1, SEQ ID NO: 2 and SEQ ID NO: 3. The lengths and the Tm values of the primers can be as follows. That is, the lengths of the primers can be, for example, from 12 bases to 40 bases (mer) and from 40 bases to 70 bases or from 16 bases to 30 bases and from 55 bases to 60 bases. Further, the lengths of primers of a primer set can be different, for example, whereas the Tm values of the primers according to some embodiments may be approximately the same or the difference between the Tm values of the primers according to some embodiments may be within 5° C.

Examples of the primer that can be used for amplification of a base sequence containing a region to which the polymorphism detection probe of the present invention hybridizes in the polymorphism detection method of the present invention are as follows. However, these are merely illustrative and do not limit the present invention.

The primer for detecting polymorphism in the 401st base (r) of the sequence indicated in SEQ ID NO: 1 may be at least one oligonucleotide selected from the group consisting of P6, P6', P7, and P7'. The hybridization and the stringent conditions are the same as those described herein. The oligonucleotides P6, P6', P7, and P7' are:

(P6) oligonucleotide having a sequence having at least 80% identity with respect to a base sequence including the 322nd to the 344th bases of the base sequence indicated in SEQ ID NO: 1 and having a length of from 23 bases to 50 bases;

(P6') oligonucleotide having a sequence being hybridized under stringent conditions with respect to a complementary strand of a base sequence including the 322nd to the 344th bases of the base sequence indicated in SEQ ID NO: 1 and having a length of from 23 bases to 50 bases;

(P7) oligonucleotide having a sequence having at least 80% identity with respect to a complementary strand of a base sequence including the 446th to the 463rd bases of the base sequence indicated in SEQ ID NO: 1 and having a length of from 18 bases to 50 bases; and (P7') oligonucleotide having a sequence being hybridized under stringent conditions with respect to a base sequence including the 446th to the 463rd bases of the base sequence indicated in SEQ ID NO: 1 and having a length of from 18 bases to 50 bases.

The oligonucleotide P6 may be oligonucleotide having a sequence having at least 80% identity with respect to a base sequence including the 322nd to the 344th bases of the base sequence indicated in SEQ ID NO: 1 and having a length of from 23 bases to 50 bases and, at the same time, may be oligonucleotide amplifying a region containing the 401st base in SEQ ID NO: 1. The oligonucleotide P6' may be oligonucleotide having a sequence being hybridized under stringent conditions with respect to a complementary strand of a base sequence including the 322nd to the 344th bases of the base sequence indicated in SEQ ID NO: 1 and having a length of from 23 bases to 50 bases and, at the same time, may be oligonucleotide amplifying a region containing the 401st base in SEQ ID NO: 1.

The oligonucleotide P7 may be oligonucleotide having a sequence having at least 80% identity with respect to a complementary strand of a base sequence including the 446th to the 463rd bases of the base sequence indicated in SEQ ID NO: 1 and having a length of from 18 bases to 50 bases and, at the same time, may be oligonucleotide amplifying a region containing the 401st base in SEQ ID NO: 1. The oligonucleotide P7' may be oligonucleotide having a sequence being hybridized under stringent conditions with respect to a base sequence including the 446th to the 463rd bases of the base sequence indicated in SEQ ID NO: 1 and having a length of from 18 bases to 50 bases and, at the same time, may be oligonucleotide amplifying a region containing the 401st base in SEQ ID NO: 1.

Examples of primers that can be used for amplifying a region containing the 401st base (r) in SEQ ID NO: 1 in the polymorphism detection method of the present invention are as follows.

```
P6 F primer (CYP3A5*3 F4)
                                   (SEQ ID NO: 14)
   5'-cgtatgtaccacccagcttaacg-3'

P7 R primer (CYP3A5*3 R4)
                                   (SEQ ID NO: 15)
   5'-cacaggagccacccaagg-3'
```

Further, for detecting polymorphism of the 401st base (r) in SEQ ID NO: 1, in some embodiments, the oligonucleotide P6 or P6' and the oligonucleotide P7 or P7' are used as a primer set.

The primer for detecting polymorphism in the 201st base(s)base(s) of the sequence indicated in SEQ ID NO: 2 may be at least one oligonucleotide selected from the group consisting of P8, P8', P9, P9', P10, and P10'. The hybridization and the stringent conditions are the same as those described herein. The oligonucleotides P8, P8', P9, P9', P10, and P10' are:

(P8) oligonucleotide having a sequence having at least 80% identity with respect to a base sequence including the 118th to the 137th bases of the base sequence indicated in SEQ ID NO: 2 and having a length of from 20 bases to 50 bases;

(P8') oligonucleotide having a sequence being hybridized under stringent conditions with respect to a complementary strand of a base sequence including the 118th to the 137th bases of the base sequence indicated in SEQ ID NO: 2 and having a length of from 20 bases to 50 bases;

(P9) oligonucleotide having a sequence having at least 80% identity with respect to a base sequence including the 22nd to the 49th bases of the base sequence indicated in SEQ ID NO: 2 and having a length of from 28 bases to 50 bases;

(P9') oligonucleotide having a sequence being hybridized under stringent conditions with respect to a complementary strand of a base sequence including the 22nd to the 49th bases of the base sequence indicated in SEQ ID NO: 2 and having a length of from 28 bases to 50 bases;

(P10) oligonucleotide having a sequence having at least 80% identity with respect to a complementary strand of a base sequence including the 292nd to the 312th bases of the base sequence indicated in SEQ ID NO: 2 and having a length of from 21 bases to 50 bases; and (P10') oligonucleotide having a sequence being hybridized under stringent conditions with respect to a base sequence including the 292nd to the 312th bases of the base sequence indicated in SEQ ID NO: 2 and having a length of from 21 bases to 50 bases.

The oligonucleotide P8 may be oligonucleotide having a sequence having at least 80% identity with respect to a base sequence including the 118th to the 137th bases of the base sequence indicated in SEQ ID NO: 2 and having a length of from 20 bases to 50 bases and, at the same time, may be oligonucleotide amplifying a region containing the 201st base in SEQ ID NO: 2. The oligonucleotide P8' may be oligonucleotide having a sequence being hybridized under stringent conditions with respect to a complementary strand of a base sequence including the 118th to the 137th bases of the base sequence indicated in SEQ ID NO: 2 and having a length of from 20 bases to 50 bases and, at the same time, may be oligonucleotide amplifying a region containing the 201st base in SEQ ID NO: 2.

The oligonucleotide P9 may be oligonucleotide having a sequence having at least 80% identity with respect to a base sequence including the 22nd to the 49th bases of the base sequence indicated in SEQ ID NO: 2 and having a length of from 28 bases to 50 bases and, at the same time, may be oligonucleotide amplifying a region containing the 201st base in SEQ ID NO: 2. The oligonucleotide P9' may be oligonucleotide having a sequence being hybridized under stringent conditions with respect to a complementary strand of a base sequence including the 22nd to the 49th bases of the base sequence indicated in SEQ ID NO: 2 and having a length of from 28 bases to 50 bases and, at the same time, may be oligonucleotide amplifying a region containing the 201st base in SEQ ID NO: 2.

The oligonucleotide P10 may be oligonucleotide having a sequence having at least 80% identity with respect to a complementary strand of a base sequence including the 292nd to the 312th bases of the base sequence indicated in SEQ ID NO: 2 and having a length of from 21 bases to 50 bases and, at the same time, may be oligonucleotide amplifying a region containing the 201st base in SEQ ID NO: 2. The oligonucleotide P10' may be oligonucleotide having a sequence being hybridized under stringent conditions with respect to a base sequence including the 292nd to the 312th bases of the base sequence indicated in SEQ ID NO: 2 and having a length of from 21 bases to 50 bases and, at the same time, may be oligonucleotide amplifying a region containing the 201st base in SEQ ID NO: 2.

Examples of primers that can be used for amplifying a region containing the 201st base(s)base(s) in SEQ ID NO: 2 in the polymorphism detection method of the present invention are as follows.

```
P8 F primer
                                   (SEQ ID NO: 16)
   5'-aggatggtaaaaaggtgctg-3'

P10 R primer
                                   (SEQ ID NO: 17)
   5'-gagagaaagaatggatccaaa-3'
```

The primer may include, for example, an additional sequence as will be described below, and examples thereof include as follows. In the sequence below, the underlined CTAGA and GACGA correspond to the additional sequence.

```
P9 F primer (CYP3A4*16-F6 + CTAGA)
                                   (SEQ ID NO: 18)
   5'-CTAGAggagtgtgatagaaggtgatctagtaga-3'

P10 R primer (U0-R3 + GACGA)
                                   (SEQ ID NO: 28)
   5'-GACGAgagagaaagaatggatccaaa-3'
```

Further, for detecting polymorphism of the 201st base(s) base(s) in SEQ ID NO: 2, in some embodiments, the oligonucleotide P8, P8', P9, or P9' and the oligonucleotide P10 or P10' are used as a primer set.

The primer for detecting polymorphism in the 501st base (r) of the sequence indicated in SEQ ID NO: 3 may be at least one oligonucleotide selected from the group consisting of P11, P11', P12, and P12'. The hybridization and the stringent conditions are the same as those described herein. The oligonucleotides P11, P11', P12, and P12' are:

(P11) oligonucleotide having a sequence having at least 80% identity with respect to a base sequence including the 432nd to the 457th bases of the base sequence indicated in SEQ ID NO: 3 and having a length of from 26 bases to 50 bases;

(P11') oligonucleotide having a sequence being hybridized under stringent conditions with respect to a complementary strand of a base sequence including the 432nd to the 457th bases of the base sequence indicated in SEQ ID NO: 3 and having a length of from 26 bases to 50 bases;

(P12) oligonucleotide having a sequence having at least 80% identity with respect to a complementary strand of a base sequence including the 508th to the 539th bases of the base sequence indicated in SEQ ID NO: 3 and having a length of from 32 bases to 50 bases; and (P12') oligonucleotide having a sequence being hybridized under stringent conditions with respect to a base sequence including the 508th to the 539th bases of the base sequence indicated in SEQ ID NO: 3 and having a length of from 32 bases to 50 bases.

The oligonucleotide P11 may be oligonucleotide having a sequence having at least 80% identity with respect to a base sequence including the 432nd to the 457th bases of the base sequence indicated in SEQ ID NO: 3 and having a length of from 26 bases to 50 bases and, at the same time, may be oligonucleotide amplifying a region containing the 501st base in SEQ ID NO: 3. The oligonucleotide P11' may be oligonucleotide having a sequence being hybridized under stringent conditions with respect to a complementary strand of a base sequence including the 432nd to the 457th bases of the base sequence indicated in SEQ ID NO: 3 and having a length of from 26 bases to 50 bases and, at the same time, may be oligonucleotide amplifying a region containing the 501st base in SEQ ID NO: 3.

The oligonucleotide P12 may be oligonucleotide having a sequence having at least 80% identity with respect to a complementary strand of a base sequence including the 508th to the 539th bases of the base sequence indicated in SEQ ID NO: 3 and having a length of from 32 bases to 50 bases and, at the same time, may be oligonucleotide amplifying a region containing the 501st base in SEQ ID NO: 3. The oligonucleotide P12' may be oligonucleotide having a sequence being hybridized under stringent conditions with respect to a base sequence including the 508th to the 539th bases of the base sequence indicated in SEQ ID NO: 3 and having a length of from 32 bases to 50 bases and, at the same time, may be oligonucleotide amplifying a region containing the 501st base in SEQ ID NO: 3.

Examples of primers that can be used for amplifying a region containing the 501st base (r) in SEQ ID NO: 3 in the polymorphism detection method of the present invention are as follows.

```
P11 F primer (CYP3A4-1B-F1)
                                (SEQ ID NO: 26)
5'-ctgtaggtgtggcttgttgggatgaa-3'

P12 R primer (CYP3A4-1B-R1)
                                (SEQ ID NO: 27)
5'-ggagccattggcataaaatctattaaatcgc-3'
```

Further, for detecting polymorphism of the 501st base (r) in SEQ ID NO: 3, in some embodiments, the oligonucleotide P11 or P11' and the oligonucleotide P12 or P12' are used as a primer set.

The oligonucleotides P6, P7, P8, P9, P10, P11, and P12 may show at least 85% identity, at least 90% identity, at least 95% identity, at least 96% identity, at least 97% identity, at least 98% identity, or at least 99% identity to a base sequence having the same bases as SEQ ID NO: 1.

The primer in the present invention may be a primer including the aforementioned oligonucleotide or may be a primer consisting of the aforementioned oligonucleotide. In the former case, for example, the primer of the present invention may include an additional sequence at at least one of the 3' end and the 5' end of the oligonucleotide. The additional sequence is not particularly limited. The additional sequence has a length of from 1, 5, or 6 base to 20 bases, from 3 bases to 15 bases, or from 5 bases to 10 bases, for example. The additional sequence contains GC at a concentration of from about 20 to 80%, from about 40 to 70%, or from about 40 to 60%, for example.

The polymorphism detection method of the present invention is not particularly limited as long as it utilizes the fluorescence labeled nucleotide as a probe. As an example of the polymorphism detection method using the fluorescence labeled nucleotide as a probe, a polymorphism detection method utilizing Tm analysis will be described below.

<Polymorphism Detection Method>

The method of detecting polymorphism in the CYP3A gene according to the present invention is a method comprising detecting polymorphism in the CYP3A gene using at least one of the aforementioned CYP3A gene polymorphism detection probes. According to the polymorphism detection method according to the present invention, the use of at least one of the aforementioned polymorphism detection probes enables a simple detection of polymorphism in the CYP3A gene with high sensitivity.

The polymorphism detection method of the present invention is a method of detecting polymorphism in the CYP3A gene, can include the following processes (I) to (IV), and also may include the following process (V). Note here that the polymorphism detection method of the present invention is characterized by using the aforementioned polymorphism detection probe, and other configurations, conditions, and the like are not limited to the description below.

The processes (I) to (V) are as follows:

(I) contacting the probe with a single-stranded nucleic acid in a sample and hybridizing the probe and the single-stranded nucleic acid to obtain a hybrid;

(II) measuring a change in a fluorescent signal based on dissociation of the hybrid by changing the temperature of the sample including the hybrid in order to dissociate the hybrid;

(III) determining a Tm value which is a temperature at which the hybrid dissociates based on the change in the fluorescent signal;

(IV) determining whether or not polymorphism of the CYP3A gene is present in the single-stranded nucleic acid in the sample based on the Tm value; and (V) determining the proportion of the single-stranded nucleic acids including polymorphism in single-stranded nucleic acids in the sample based on the presence or absence of polymorphism.

Further, in addition to the processes (I) to (IV) or the processes (I) to (V), the present invention may include the process of amplifying the nucleic acid before (I) or at the same time as (I). Here, determining the Tm value in (III) may not only include measuring the dissociation temperature of a hybrid but may also include measuring the level of the differential value of the fluorescence signal that changes in response to a temperature.

In the present invention, the nucleic acid in the sample may be a single-stranded nucleic acid or a double-stranded nucleic acid. In the case where the nucleic acid is a double-stranded nucleic acid, for example, the method according to some embodiments include melting (dissociating) the double-stranded nucleic acid in the sample into single-stranded nucleic acids by heating prior to the hybridization with the labeled oligonucleotide. The dissociation of the double-stranded nucleic acid into single-stranded nucleic acids enables the hybridization with the labeled oligonucleotide.

In the present invention, the nucleic acid to be detected contained in the sample can be a nucleic acid inherently contained in a biological sample, for example. In some embodiments, since the detection accuracy can be improved, the nucleic acid to be detected is an amplification product obtained by amplifying a region containing a mutated site of the CYP3A gene by an amplification method such as PCR using the nucleic acid inherently contained in a biological sample as a template. The length of the amplification product is not particularly limited, and is, for example, from 50 bases to 1000 bases (mer), or from 80 bases to 200 bases. Further, the nucleic acid in the sample can be, for example, cDNA that is synthesized from RNA (total RNA, mRNA, or the like) derived from a biological sample by reverse transcription PCR (RT-PCR).

In the present invention, there is no particular limitation on the addition ratio (molar ratio) of the polymorphism detection probe of the present invention relative to the nucleic acid in the sample. In one aspect, the addition ratio (molar ratio) of the polymorphism detection probe of the present invention relative to DNA in the sample is no more than 1 times. In another aspect, in light of ensuring a sufficient detection signal, the addition ratio (molar ratio) of the polymorphism detection probe of the present invention relative to the nucleic acid in the sample can be no more than 0.1 times. Here, the nucleic acid in the sample may be a total of the nucleic acid to be detected in which the polymorphism to be detected is generated and the nucleic acid not to be detected in which the polymorphism is not generated; or the nucleic acid in the sample may be a total of the amplification product including the sequence to be detected in which the polymorphism to be detected is generated and the amplification product including the sequence not to be detected in which the polymorphism is not generated. In some embodiments, although the ratio of the nucleic acid to be detected in nucleic acids in the sample is normally unknown, as a result, the addition ratio (molar ratio) of the polymorphism detection probe relative to the nucleic acid to be detected (the amplification product including the sequence to be detected) can be no more than 10 times. Further, in some embodiments, the addition ratio (molar ratio) of the polymorphism detection probe relative to the nucleic acid to be detected (the amplification product including the sequence to be detected) can be no more than 5 times or no more than 3 times. There is no particular lower limitation on the addition ratio (molar ratio) of the polymorphism detection probe, and for example, it can be, at least 0.001 times, at least 0.01 times, or at least 0.1 times.

The addition ratio of the polymorphism detection probe of the present invention relative to DNA may be a molar ratio relative to a double-stranded nucleic acid or a molar ratio relative to a single-stranded nucleic acid, for example.

In the present invention, on the basis of the aforementioned principle, the measurement of the change in the signal in relation to a temperature change for determining the Tm value can be performed by measuring absorbance at 260 nm. In some embodiments, measured is the signal based on the signal of the labeling substance added to the polymorphism detection probe, which is the signal that changes depending on the status of the hybrid of the single-stranded DNA and the polymorphism detection probe. Therefore, the aforementioned labeled oligonucleotides may be used as the polymorphism detection probe. The aforementioned labeled oligonucleotides include, for example, the fluorescently labeled oligonucleotide in which the fluorescence intensity when hybridized to its target sequence (complementary sequence) is smaller (quenched) than the fluorescence intensity when not hybridized to its target sequence; and the fluorescently labeled oligonucleotide in which fluorescence intensity when hybridized to its target sequence is larger than the fluorescence intensity when not hybridized to its target sequence.

For example, although the probe of the former type does not emit a fluorescence signal or emits a weak fluorescence signal when it forms the hybrid (double-stranded DNA) with the sequence to be detected, the fluorescence signal is emitted or increased when the probe is dissociated by heating. Further, for example, the probe of the latter type emits a fluorescence signal when it forms the hybrid (double-stranded DNA) with the sequence to be detected, and the fluorescence signal is decreased (quenched) when the probe is dissociated by heating. Accordingly, by detecting the change in the fluorescence signal based on a fluorescence labeling under the conditions (fluorescence wavelength and the like) specific to the fluorescence labeling, progress of the melting of the hybrid and the Tm value can be determined as in the case of the measurement of an absorbance at 260 nm.

Next, with respect to the polymorphism detection method of the present invention, the method of detecting the change in a signal based on a fluorescent dye will be described with reference to the specific examples. Note here that the polymorphism detection method of the present invention is characterized by using the aforementioned polymorphism detection probe, and other processes, conditions, and the like are not limited.

The sample containing a nucleic acid that is used as a template when nucleic acid amplification is performed is not particularly limited as long as it contains a nucleic acid, especially, the CYP3A gene. Examples thereof include samples that are derived from or can be derived from arbitrary biological origins such as tissues such as large intestine and lung; a blood cell such as leukocyte; whole blood; blood plasma; expectoration; oral mucosa suspension; somatic cells such as nail and hair; germ cell; milk; ascites; paraffin-embedded tissue; gastric juice; fluid obtained by gastric lavage; urine; peritoneal fluid; amniotic fluid; and cell culture. The method of collecting a sample and the method of preparing a sample containing a nucleic acid are not particularly limited and conventionally known methods can be employed. Further, the nucleic acid serving as a template can directly be used just as it is obtained from the origin or can be used after applying pretreatment for modifying the properties of the sample. For example, in the case where whole blood is used as a sample, isolation of genomic DNA from the whole blood can be performed by a conventionally known method. For example, a commercially available genomic DNA isolation kit (product name: GFX Genomic Blood DNA Purification kit, produced by GE Healthcare Biosciences) or the like can be used.

Next, the polymorphism detection probe including the aforementioned labeled oligonucleotide is added to a sample containing isolated genomic DNA. The polymorphism detection probe may be added to the liquid sample containing the isolated genomic DNA or may be mixed with the genomic DNA in an appropriate solvent. The solvent is not particularly limited, and examples thereof include known solvents such as a buffering solution such as Tris-HCl; a solvent containing KCl, $MgCl_2$, $MgSO_4$, glycerol, or the like; and a PCR reaction solution.

There is no particular limitation on the timing of addition of the polymorphism detection probe, and for example, in the case where the amplification such as PCR that will be described below is performed, the polymorphism detection probe may be added after the amplification to the PCR amplification product or may be added before the amplification. In the case where the detection probe is added before the amplification such as PCR, for example, a fluorescent dye or a phosphate group may be added to the 3' end of the detection probe as described herein.

As the method of amplifying a nucleic acid, for example, a method using polymerase can be employed. Examples thereof include a PCR method, an ICAN method, a LAMP method, and a NASBA method. In the case where a nucleic acid is amplified by the method using polymerase, in some embodiments, amplification is performed in the presence of the probe of the present invention probe. It is easy for those skilled in the art to adjust reaction conditions or the like for the amplification according to the probe and polymerase used. Thereby, since polymorphism can be evaluated simply by analyzing the Tm value of the probe after amplification of the nucleic acid, there is no need to handle the amplification product after the completion of the reaction. Therefore, there is no worry about contamination by the amplification product. Further, since the detection can be performed with the same equipment as that required for amplification, there is no need to transfer a container and automatization can be done easily.

Further, as DNA polymerase used for the PCR method, commonly-used DNA polymerase can be used with no particular limitation. Examples of the DNA polymerase include GeneTaq (produced by NIPPON GENE CO., LTD.), Prime-STAR Max DNA Polymerase (produced by TAKARA BIO INC.), and Taq polymerase. There is no limitation on the amount of the polymerase to be used, and a commonly-used concentration can be employed. For example, in the case where Taq polymerase is used, the concentration of the polymerase can be from 0.01 U to 100 U with respect to 50 µl of a reaction solution. Thereby, there is a tendency that the detection sensitivity to the CYP3A polymorphism is increased.

Further, the PCR method can be performed by appropriately selecting commonly-used conditions. Here, at the time of the amplification, for example, the number of copies of DNA (the sequence to be detected) contained in the sample can be determined by monitoring the amplification by real-time PCR. In other words, since the proportion of the probe that forms a hybrid increases in accordance with the amplification of DNA (the sequence to be detected) by PCR, the fluorescence intensity changes. By monitoring this change, the number of copies and the proportion of the sequence to be detected (normal DNA or mutated DNA) contained in the sample can be evaluated.

In the polymorphism detection method of the present invention, the labeled oligonucleotide and the single-stranded nucleic acid in the sample are brought into contact to hybridize. The single-stranded nucleic acid in the sample can be prepared, for example, by dissociating the PCR amplification product obtained in the manner described herein.

There is no limitation on the heating temperature in the dissociation (dissociation process) of the PCR amplification product, and an example thereof includes a temperature at which the amplification product can be dissociated. The temperature is, for example, 85 to 95° C. Furthermore, there is no particular limitation on the heating time, and heating time is, for example, 1 second to 10 minutes, or 1 second to 5 minutes.

The hybridization between the dissociated single-stranded DNA and the labeled oligonucleotide may be performed by decreasing the heating temperature employed in the dissociation process after the dissociation process, for example. The temperature condition is, for example, 40 to 50° C.

The volume and the concentration of each composition in the reaction solution of the hybridization process are not particularly limited. Specific examples are as follows. The DNA concentration in the reaction solution can be, for example, 0.01 µmol/L to 1 µmol/L or 0.1 µmol/L to 0.5 µmol/L. The concentration of the labeled oligonucleotide is, for example, in the range satisfying the addition ratio to the DNA, and is, for example, 0.001 µmol/L to 10 µmol/L or 0.001 µmol/L to 1 µmol/L.

Further, the obtained hybrid of the single-stranded DNA and the fluorescently labeled oligonucleotide is gradually heated to thereby measure the change in the fluorescence signal associated with the temperature increase. For example, when a QProbe is used, the fluorescence intensity in a hybridized state with the single-stranded DNA is smaller (or quenched) than a dissociated state. Therefore, for example, the hybrid that exhibits decreasing (or quenching) fluorescence is gradually heated to thereby measure the increase in the fluorescence intensity associated with the temperature increase.

There is no particular limitation on the temperature range when measuring the change in the fluorescence intensity, and the initial temperature can be, for example, from room temperature to 85° C. or from 25 to 70° C. The final temperature can be, for example, from 40 to 105° C. Furthermore, there is no particular limitation on the temperature increase rate, and it can be, for example, from 0.1 to 20° C./sec or from 0.3 to 5° C./sec.

Next, the Tm value is determined by analyzing the change in the signal. Specifically, the differential value for each temperature (−d fluorescence intensity/dt) is calculated from the resulting fluorescent intensity and the temperature that shows the lowest value is determined as the Tm value. Further, the highest point in the fluorescent intensity increase amount per unit time (fluorescent intensity increase amount/t) can be determined as the Tm value. In contrast, the decrease amount in the fluorescent intensity may be measured when the labeled probe is not a quenching probe but rather a probe in which the signal intensity increases when forming a hybrid.

Further, in the present invention, as described herein, the hybrid is heated to thereby measure the change in the fluorescence signal (in some embodiments, the increase in the fluorescence intensity) associated with the temperature increase as described. In substitution for this method, for example, measurement of the change in the signal at the time of hybrid formation may be performed. That is, the temperature of the sample to which the probe is added is decreased to thereby form a hybrid, and then the change in the fluorescence signal associated with the temperature decrease is measured.

In an actual example, in the case where a Quenching Probe (QProbe) is used, although the fluorescence intensity when the probe is added to the sample is large because the probe is in a dissociated state, the fluorescence is decreased (or quenched) when a hybrid is formed due to a decrease in the temperature.

Therefore, for example, the decrease in the fluorescent intensity associated with the temperature decrease may be measured by gradually decreasing the temperature of the sample heated. On the other hand, in the case where a labeled probe that exhibits increasing signal when forming a hybrid is used, although the fluorescence intensity when the probe is added to the sample is small (or quenched) because the probe is in a dissociated state, the fluorescence intensity is increased when a hybrid is formed due to a decrease in the temperature. Therefore, for example, the increase in the fluorescent intensity associated with the temperature decrease may be measured by gradually decreasing the temperature of the sample.

In the polymorphism detection method of the present invention, for example, one of the polymorphism detection probes may be used alone or two or more of them may be used in combination. The type of the polymorphism detection probe to be used can be decided suitably according to the polymorphism to be detected. In the present invention, for example, only the CYP3A5*3 polymorphism, only the CYP3A4*16 polymorphism, or only the CYP3A4*1B polymorphism may be detected, or two of them or three of them can be detected in one reaction system. Further, at least one of the CYP3A5*3 polymorphism, the CYP3A4*16 polymorphism, and the CYP3A4*1B polymorphism and polymorphism other than these can be detected in one reaction system.

In the polymorphism detection method of the present invention, in the case where two or more of the polymorphism detection probes are used, for example, the probes may be labeled probes including fluorescent dyes different from one another. The different fluorescent dyes include, for example, fluorescent dyes having different detection conditions from one another.

The method of detecting plural genetic polymorphisms in the same system is not particularly limited. For example, the probes capable of detecting the respective polymorphisms may be preliminarily mixed and then added to the sample, or the probes capable of detecting the respective polymorphisms may be added continuously to the sample containing a single-stranded nucleic acid. Here, the "system" refers to an independent reaction system composed of a sample containing a hybrid in which an oligonucleotide and a single-stranded nucleic acid are hybridized.

<Drug Efficacy Determination Method>

The drug efficacy determination method of the present invention includes: detecting polymorphism in the CYP3A gene by the aforementioned polymorphism detection method; and determining tolerance to the drug or the efficacy of the drug based on the detection result.

According to the polymorphism detection method, the use of the polymorphism detection probe of the present invention enables a simple detection of polymorphism in the CYP3A gene with high sensitivity. Therefore, on the basis of the polymorphism in the CYP3A gene, the simple determination of the drug efficacy can be performed with high sensitivity.

Further, on the basis of the presence or absence of polymorphism and the abundance ratio between a mutated sequence and a normal sequence, the tolerance to the drug or the efficacy of the drug can be determined. Further, the drug efficacy determination method of the present invention is effective for deciding therapeutic strategies such as the increase in dose of a drug and the change of the drug to another therapeutic drug based on the presence or absence of polymorphism and the abundance ratio between a mutated sequence and a normal sequence. Examples of the drug to be determined include an immunosuppressant, a molecular target drug, and an antidepressant. Among them, the immunosuppressant and the molecular target drug are particularly used. A specific example of the drug includes an immunosuppressant such as tacrolimus.

<Polymorphism Detection Reagent Kit>

The CYP3A gene polymorphism detection reagent kit for detecting polymorphism in the CYP3A gene of the present invention includes the aforementioned polymorphism detection probe. There is a tendency that the polymorphism detection reagent kit can perform, for example, a simple detection of polymorphism in the CYP3A gene by including at least one of the aforementioned polymorphism detection probes that can perform a simple and highly sensitive detection of polymorphism in the 401st base of the sequence indicated in SEQ ID NO: 1, polymorphism in the 201st base of the sequence indicated in SEQ ID NO: 2, and/or polymorphism in the 501st base of the sequence indicated in SEQ ID NO: 3 among the CYP3A gene.

Further, the polymorphism detection reagent kit of the present invention may further include a primer for amplifying a sequence containing the CYP3A gene polymorphism to be detected. Thereby, the polymorphism detection reagent kit of the present invention can detect polymorphism in the CYP3A gene with high accuracy. Note here that the matters described above can be applied to the probe and the primer that can be contained in the polymorphism detection reagent kit.

In the case where two or more fluorescently labeled oligonucleotides are contained as the polymorphism detection probe, the respective fluorescently labeled oligonucleotides may be contained in a mixed state or may be contained separately. Further, in the case where two or more of the probes of the present invention are contained in a mixed state and in the case where the Tm analysis of the respective fluorescently labeled oligonucleotides and the respective sequences to be detected is performed in the same reaction system in use although two or more of the probes of the present invention are contained separately, two or more probes may be labeled with fluorescent dyes having emission wavelengths different from one another. By changing the type of the fluorescent material in this manner, detection with respect to the respective probes can be performed in the same reaction system.

Further, in addition to the probe, the detection reagent kit of the present invention can further include a reagent(s) required for amplifying nucleic acid in the detection method of the present invention. The probe, the primer, and other reagents may be contained separately or some of them may be contained as a mixture.

Here, with respect to the expression, "contained separately", the components are not necessarily contained in separate containers that can be handled independently as long as the respective reagents are divided so that the reagents are not brought into contact one another.

For example, by including a primer set for amplifying the sequence containing a polymorphism site (a region to which a probe is hybridized), the detection reagent kit of the present invention can detect polymorphism with higher sensitivity.

Further, in some embodiments, the polymorphism detection reagent kit of the present invention includes an instruction manual. Examples of the instruction manual include: an instruction manual describing that the mutation in the CYP3A gene is detected using the aforementioned polymorphism detection probe by making the differential melting curve with respect to a sample containing the nucleic acid to be detected and analyzing the Tm value; and an instruction manual describing various reagents that are contained or that can be additionally contained in the detection reagent kit.

EXAMPLES

Examples of the present invention will be described below. However, the present invention is not limited by the following Examples.

Example 1

In this Example, Tm analysis was performed in the common presence of a wild type nucleic acid to be detected and a mutant type nucleic acid to be detected to detect the CYP3A5*3 polymorphism and the CYP3A4*16 polymorphism in the CYP3A gene.

Diluted blood, the entire genetic material of a cell (purified genome), and a plasmid are prepared as nucleic acid samples.

The diluted blood was prepared as follows. That is, 10 μL of whole blood collected with an EDTA blood collection tube and 70 μL of the diluent 1 summarized in the following Table 2 were mixed to prepare a mixture. Then, 10 μL of the mixture and 70 μL of the diluent 2 summarized in the following Table 2 were mixed and the resultant was heated at 95° C. for 10 minutes. In the nucleic acid to be detected contained in the whole blood, the CYP3A5*3 polymorphism is a heterozygote of a wild type and a mutant type and the CYP3A4*16 polymorphism is a homozygote of wild types. The purified genome was prepared by a routine method from whole blood. In the purified genome, the CYP3A5*3 polymorphism is a homozygote of mutant types and the CYP3A4*16 polymorphism is a homozygote of wild types. As the plasmid, the CYP3A4*16 mutant type plasmid that includes a partial sequence of the CYP3A4 gene by insertion of the oligonucleotide having a sequence including the 1st to 411th bases in SEQ ID NO: 2 was prepared. In the CYP3A4*16 mutant type plasmid, the 201st base(s)base(s) in SEQ ID NO: 2 is guanine (g).

TABLE 2

| (Diluent 1: 70 μl) |
| --- |
| 10 mmol/L Tris-HCl (pH 8.0) |
| mmol/L EDTA (pH 8.0) |
| 0.3 w/v % SDS |
| (Diluent 2: 70 μl) |
| 10 mmol/L Tris-HCl (pH 8.0) |
| 0.1 mmol/L EDTA (pH 8.0) |

The nucleic acid samples were mixed at the following ratios to prepare the samples 1 to 4.
(Sample)

| Sample No. | Diluted blood | Purified genome | CYP3A4*16 mutant type plasmid |
| --- | --- | --- | --- |
| 1 | 100% | 0% | 0% |
| 2 | 0% | 100% | 0% |
| 3 | 0% | 50% | 50% |
| 4 | 0% | 0% | 100% |

50 μL of PCR reaction mixtures respectively containing the aforementioned samples were prepared. Each of the PCR reaction mixtures was prepared by mixing 4 μL of the sample and the components of the PCR reaction solution summarized in the following Table 3 at the following concentrations. PCR and Tm analysis were performed in relation to the PCR reaction mixtures using a fully automated SNPs inspection device (product name: i-densy® IS-5310, produced by Arkray Inc.). Conditions for PCR were as follows. That is, after the PCR reaction mixture was treated at 95° C. for 1 minute, one cycle of treatment at 95° C. for 1 second and 56° C. for 15 seconds was repeated for 50 cycles. Further, the reaction mixture was treated at 95° C. for 1 second and 40° C. for 60 seconds. Thereafter, the reaction solution was heated from 40° C. to 75° C. at the temperature rise rate of 1° C./3 seconds to thereby perform Tm analysis by measurement of the change in the fluorescence intensity over time at a detection wavelength according to a fluorescent dye. Further, as a control, PCR and Tm analysis were performed in the same manner as described above except that the diluent 2 was used instead of the sample. The detection wavelength for BODIPY FL was 520 to 555 nm and the detection wavelength for TAMRA was 585 to 700 nm (hereinafter, the same applies).

TABLE 3

| 1 × PCR reaction buffer |
| --- |
| 1.88 U Taq polymerase |
| 1.5 mmol/L MgCl$_2$ |
| 0.2 mmol/L dNTP |
| 0.5 μmol/L CYP3A5*3 F primer |
| 1 μmol/L CYP3A5*3 R primer |
| 2 μmol/L CYP3A4*16 F primer |
| 1 μmol/L CYP3A4*16 R primer |
| 0.1 μmol/L CYP3A5*3 probe |
| 0.4 μmol/L CYP3A4*16 probe |

The sequences of the CYP3A5*3 primer and the CYP3A4*16 primer are as follows.

```
(CYP3A5*3 primer)
F primer (CYP3A5*3 F4)
                              (SEQ ID NO: 14)
5'-cgtatgtaccacccagcttaacg-3'

R primer (CYP3A5*3 R4)
                              (SEQ ID NO: 15)
5'-cacaggagccacccaagg-3'

(CYP3A4*16 primer)
F primer (UO-F2)
                              (SEQ ID NO: 16)
5'-aggatggtaaaaaggtgctg-3'

R primer (UO-R3)
                              (SEQ ID NO: 17)
5'-gagagaaagaatggatccaaa-3'
```

The CYP3A5*3 probe that was used is the CYP3A5*3 mutant type probe having the sequence below. The CYP3A5*3 probe is a mutant type probe for an antisense strand of the mutant type CYP3A5 gene. In the sequence below, the base that is underlined is a base that shows identity with respect to the CYP3A5*3 mutant type sequence. The CYP3A5*3 probe was labeled with a fluorescent dye BODIPY FL at the 3' end. The CYP3A4*16 probe that was used is the CYP3A4*16 mutant type probe having the sequence below. The CYP3A4*16 probe is a mutant type probe for a sense strand of the mutant type CYP3A4 gene. In the sequence, the base that is underlined is a base that is complementary to the CYP3A4*16 mutant type sequence. The CYP3A4*16 probe was labeled with a fluorescent dye TAMRA at the 3' end.

```
CYP3A5*3 probe (3FL-CYP3A5*3-mt-F1-21)
                              (SEQ ID NO: 4)
5'-ttgtctttcaGtatctcttcc-(BODIPY FL)-3'

CYP3A4*16 probe (UO-3TMR4)
                              (SEQ ID NO: 10)
5'-atgatgTgctaCtgatcacatccatgc-(TAMRA)-3'
```

Figure 2A:
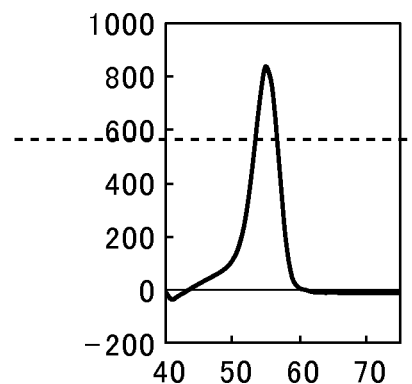
FIGS. 2A and 2B show melting curves of another sample according to Example 1 of the present invention.
Figure 2B:
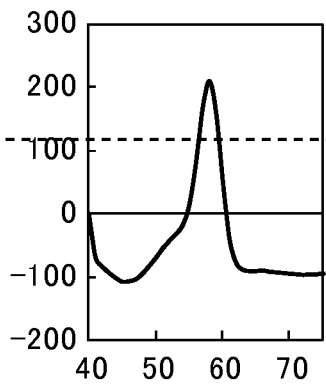
Figure 3A:
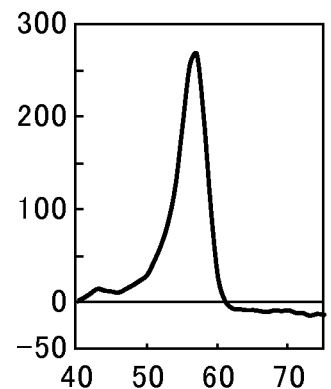
FIGS. 3A and 3B show melting curves of yet another sample according to Example 1 of the present invention.
Figure 3B:
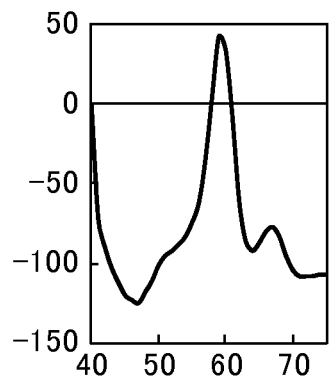
Figure 4:
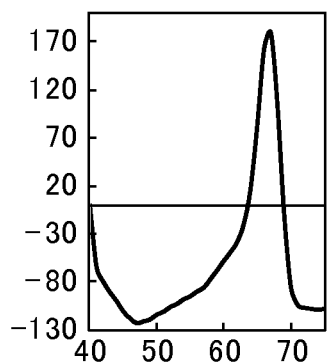
FIG. 4 shows a melting curve of still another sample according to Example 1 of the present invention.
Figure 5A:
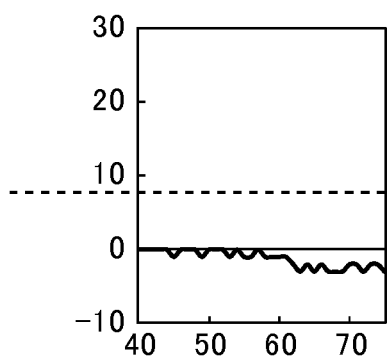
FIGS. 5A and 5B show melting curves of still another sample according to Example 1 of the present invention.
Figure 5B:
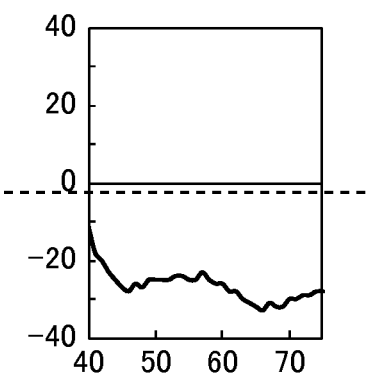

The results are illustrated in FIGS. 1(A) to 5(B). FIGS. 1(A) to 5(B) are graphs of the Tm analysis showing the change in the fluorescent intensity associated with temperature rise. FIGS. 1(A) and 1(B) show the results of the sample 1, FIGS. 2(A) and 2(B) show the results of the sample 2, FIGS. 3(A) and 3(B) show the results of the sample 3, FIG. 4 shows the result of the sample 4, and FIGS. 5(A) and 5(B) show the results of the control. In FIGS. 1(A) to 3(B) and 5(A) and 5(B), (A) shows a melting curve with respect to the CYP3A5*3 probe and (B) shows a melting curve with respect to the CYP3A4*16 probe. FIG. 4 shows a melting curve with respect to the CYP3A4*16 probe. The horizontal axis shows the temperature (° C.) during measurement. The vertical axis shows the change in the fluorescent intensity (hereinafter, this is also referred to as "fluorescent change amount"), and the unit was "d fluorescence intensity increase amount/dt" (dF/dt). The Tm value of the CYP3A5*3 probe and the CYP3A5*3 wild type is in proximity to 49° C. and the Tm value of the CYP3A5*3 probe and the CYP3A5*3 mutant type is in proximity to 56° C. The Tm value of the CYP3A4*16 probe and the CYP3A4*16 wild type is in proximity to 59° C. and the Tm value of the CYP3A4*16 probe and the CYP3A4*16 mutant type is in proximity to 67° C.

Figure 1B:
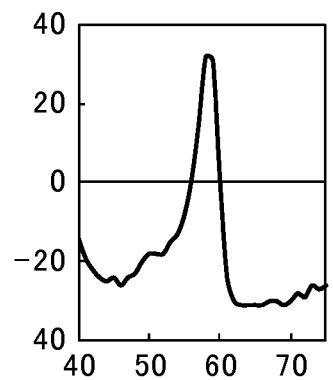

As illustrated in FIG. 1(A), with respect to the CYP3A5*3 polymorphism, the sample 1 containing the CYP3A5*3 polymorphism as a heterozygote of a wild type and a mutant type showed peaks at the Tm value in relation to a wild type and the Tm value of a mutant type. As illustrated in FIG. 1(B), with respect to the CYP3A4*16 polymorphism, the sample 1 containing the CYP3A4*16 polymorphism as a homozygote of wild types showed a peak only at the Tm value in relation to a wild type.

As illustrated in FIG. 2(A), with respect to the CYP3A5*3 polymorphism, the sample 2 containing the CYP3A5*3 polymorphism as a homozygote of mutant types showed a peak only at the Tm value in relation to a mutant type. As illustrated in FIG. 2(B), with respect to the CYP3A4*16 polymorphism, the sample 2 containing the CYP3A4*16 polymorphism as a homozygote of wild types showed a peak only at the Tm value in relation to a wild type.

As illustrated in FIG. 3(A), with respect to the CYP3A5*3 polymorphism, the sample 3 containing the CYP3A5*3 polymorphism as a homozygote of mutant types showed a peak only at the Tm value in relation to a mutant type. As illustrated in FIG. 3(B), with respect to the CYP3A4*16 polymorphism, the sample 3 containing the CYP3A4*16 polymorphism contained in the purified genome as a wild type and containing the CYP3A4*16 polymorphism contained in the plasmid as a mutant type showed peaks at the Tm value in relation to a wild type and the Tm value in relation to a mutant type.

As illustrated in FIG. 4, with respect to the CYP3A4*16 polymorphism, the sample 4 containing the CYP3A4*16 polymorphism as a homozygote of mutant types showed a peak only at the Tm value in relation to a mutant type. The sample 4 that does not include a base sequence of a region containing the CYP3A5*3 polymorphism did not show a peak with respect to the CYP3A5*3 polymorphism.

As illustrated in FIGS. 5(A) and 5(B), the diluent 2, which is a control, did not show a peak with respect to both of the CYP3A4*16 polymorphism and the CYP3A5*3 polymorphism.

Example 2

In this Example, Tm analysis was respectively performed in relation to a wild-type artificial nucleic acid and a mutant-type artificial nucleic acid to detect the polymorphism (CYP3A4*16) in the CYP3A gene using a probe that hybridizes to an antisense strand.

A mutant type artificial nucleic acid (mt) and a wild type artificial nucleic acid (wt) that are complementary to the 173st to 222nd bases in SEQ ID NO: 2 as illustrated in the sequences below were prepared. In the sequences below, the underlined bases correspond to the 201st base in SEQ ID NO: 2. The respective artificial nucleic acids were adjusted to 0.1 μmol/L and were used as samples.

mt
(SEQ ID NO: 19)
Ttcactccaratgatgtgcta<u>C</u>tgatcacatccatgctgtaggccccaaa wt
(SEQ ID NO: 20)
ttcactccaratgatgtgcta<u>G</u>tgatcacatccatgctgtaggccccaaa 50 μL of reaction mixtures respectively containing the aforementioned samples were prepared. Each of the reaction mixtures was prepared by mixing the components of the reaction solution summarized in the following Table 4 at the following concentrations. Tm analysis was performed in relation to the reaction mixtures using a fully automated SNPs inspection device (product name: i-densy® IS-5310, produced by Arkray Inc.). After treating at 95° C. for 1 second and 40° C. for 60 seconds, the reaction solution was heated from 40° C. to 75° C. at the temperature rise rate of 1° C./3 seconds to thereby perform Tm analysis by measurement of the change in the fluorescence intensity over time at a detection wavelength according to a fluorescent dye.

TABLE 4

| 1 × reaction buffer |
| --- |
| 1.88 U Taq polymerase |
| 1.5 mmol/L MgCl$_2$ |
| 0.2 mmol/L dNTP |
| 0.2 mmol/L probe |
| 0.2 mmol/L sample |

The probe that was used is the CYP3A4*16 mutant type probe having the sequence below. The probe is a mutant type probe for an antisense strand of the mutant type CYP3A4 gene. In the sequence below, the base that is underlined is a base that shows identity with respect to the CYP3A4*16 mutant type sequence. The probe was labeled with a fluorescent dye TAMRA at the 3' end.

CYP3A4*16 mutant type probe (3T-CYP3A4*16-MF1)
(SEQ ID NO: 6)
5'-gatgtgatca<u>g</u>tagc-(TAMRA)-3'

Figure 6A:
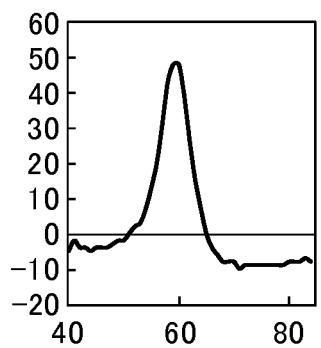
FIGS. 6A and 6B show melting curves of a sample according to Example 2 of the present invention.
Figure 6B:
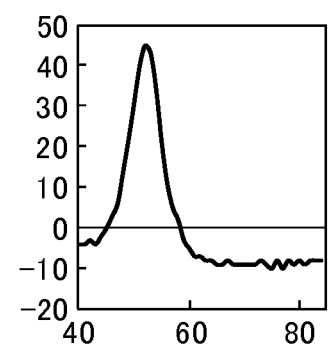

The results are illustrated in FIGS. 6(A) and 6(B). FIGS. 6(A) and 6(B) are graphs of the Tm analysis showing the change in the fluorescent intensity associated with temperature rise. In FIGS. 6(A) and 6(B), (A) shows the result for mt 100% and (B) shows the result for wt 100%. The horizontal axis shows the temperature (° C.) during measurement. The vertical axis shows the change in the fluorescent intensity (hereinafter, this is also referred to as "fluorescent change amount"), and the unit was "d fluorescence intensity increase amount/dt" (dF/dt). The Tm value of the CYP3A4*16 mutant type probe and mt is in proximity to 60° C. and the Tm value of the CYP3A4*16 mutant type probe and wt is in proximity to 53° C.

As illustrated in FIG. 6(A), with respect to mt, the sample showed a peak only at the Tm value in relation to mt. On the other hand, as illustrated in FIG. 6(B), with respect to wt, the sample showed a peak only at the Tm value in relation to wt.

Example 3

In this Example, Tm analysis was respectively performed in relation to a wild-type artificial nucleic acid and a mutant-type artificial nucleic acid to detect the polymorphism (CYP3A4*16) in the CYP3A gene using a probe that hybridizes to a sense strand. Tm analysis was performed in the same manner as in Example 2 except that the wild type artificial nucleic acid and the mutant type artificial nucleic acid described below and the CYP3A4*16 mutant type probe were used.

A mutant type artificial nucleic acid (mt) and a wild type artificial nucleic acid (wt) that correspond to the 173st to 222nd bases in SEQ ID NO: 2 as illustrated in the sequences below were prepared. In the sequences below, the underlined bases correspond to the 201st base in SEQ ID NO: 2. The respective artificial nucleic acids were adjusted to 0.1 μmol/L and were used as samples.

mt
(SEQ ID NO: 21)
tttggggcctacagcatggatgtgatcaGtagcacatcatytggagtgaa wt
(SEQ ID NO: 22)
tttggggcctacagcatggatgtgatcaCtagcacatcatytggagtgaa The probe that was used is the CYP3A4*16 mutant type probe having the sequence below. The probe is a mutant type probe for a sense strand of the mutant type CYP3A4 gene. In the sequence below, the base that is underlined is a base that is complementary to the CYP3A4*16 mutant type sequence. The probe was labeled with a fluorescent dye TAMRA at the 3' end.

CYP3A4*16 probe (3T-CYP3A4*16-MR1)
(SEQ ID NO: 8)
5'-tgtgctactgatcacatcc-(TAMRA)-3'

Figure 7A:
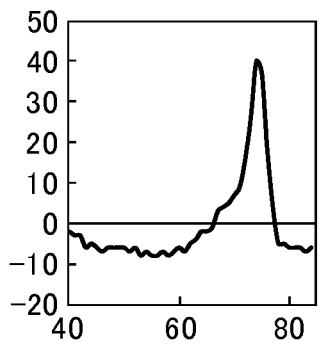
FIGS. 7A and 7B show melting curves of a sample according to Example 3 of the present invention.
Figure 7B:
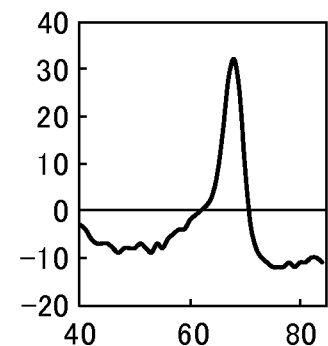

The results are illustrated in FIGS. 7(A) and 7(B). FIGS. 7(A) and 7(B) are graphs of the Tm analysis showing the change in the fluorescent intensity associated with temperature rise. In FIGS. 7(A) and 7(B), (A) shows the result for mt 100% and (B) shows the result for wt 100%. The horizontal axis shows the temperature (° C.) during measurement. The vertical axis shows the change in the fluorescent intensity (hereinafter, this is also referred to as "fluorescent change amount"), and the unit was "d fluorescence intensity increase amount/dt" (dF/dt). The Tm value of the CYP3A4*16 mutant type probe and mt is in proximity to 75° C. and the Tm value of the CYP3A4*16 mutant type probe and wt is in proximity to 68° C.

As illustrated in FIG. 7(A), with respect to mt, the sample showed a peak only at the Tm value in relation to mt. On the other hand, as illustrated in FIG. 7(B), with respect to wt, the sample showed a peak only at the Tm value in relation to wt.

Comparative Example 1

In this Comparative Example, Tm analysis was respectively performed in relation to a wild-type artificial nucleic acid and a mutant-type artificial nucleic acid to detect the polymorphism (CYP3A5*3) in the CYP3A gene using a probe that hybridizes to a sense strand. Tm analysis was performed in the same manner as in Example 2 except that the wild type artificial nucleic acid and the mutant type artificial nucleic acid described below and the CYP3A5*3 mutant type probe were used.

A mutant type artificial nucleic acid (mt) and a wild type artificial nucleic acid (wt) that correspond to the 379th to 428th bases in SEQ ID NO: 1 as illustrated in the sequences below were prepared. In the sequences below, the underlined bases correspond to the 401st base in SEQ ID NO: 1. The respective artificial nucleic acids were adjusted to 0.1 μmol/L and were used as samples.

mt
(SEQ ID NO: 23)
taaagagctcttttgtctttcaAtatctcttccctgtttggaccacatta wt
(SEQ ID NO: 24)
taaagagctcttttgtctttcaGtatctcttccctgtttggaccacatta The probe that was used is the CYP3A5*3 mutant type probe having the sequence below. The probe is a mutant type probe for a sense strand of the mutant type CYP3A5 gene. In the sequence below, the base that is underlined is a base that is complementary to the CYP3A5*3 mutant type sequence. The CYP3A5*3 mutant type probe was labeled with a fluorescent dye TAMRA at the 3' end.

CYP3A5*3 mutant type probe (5T-CYP3A5*3-mt-R1-22)
(SEQ ID NO: 25)
5'-(TAMRA)-cagggaagagataCtgaaagac-P-3'

Figure 8A:
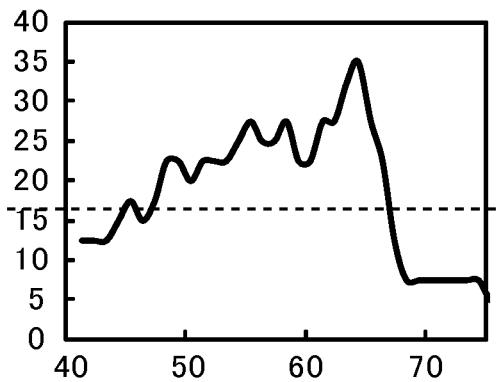
FIGS. 8A and 8B show melting curves of a sample according to Comparative Example 1.
Figure 8B:
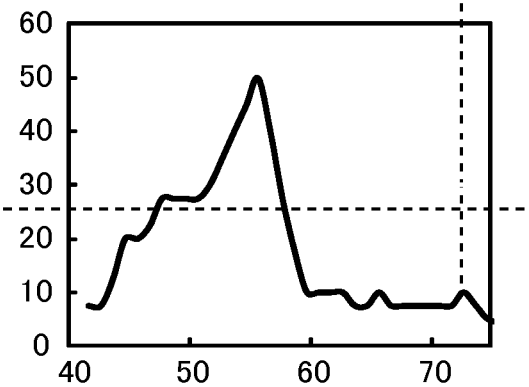

The results are illustrated in FIGS. 8(A) and 8(B). FIGS. 8(A) and 8(B) are graphs of the Tm analysis showing the change in the fluorescent intensity associated with temperature rise. In FIGS. 8(A) and 8(B), (A) shows the result for mt 100% and (B) shows the result for wt 100%. The horizontal axis shows the temperature (° C.) during measurement. The vertical axis shows the change in the fluorescent intensity (hereinafter, this is also referred to as "fluorescent change amount"), and the unit was "d fluorescence intensity increase amount/dt" (dF/dt).

As illustrated in FIGS. 8(A) and 8(B), the sample did not show a clear peak with respect to both wt and mt.

Comparative Example 2

In this Comparative Example, Tm analysis was respectively performed in relation to a wild-type artificial nucleic acid and a mutant-type artificial nucleic acid to detect the polymorphism (CYP3A4* 16) in the CYP3A gene using a probe that hybridizes to a sense strand. Tm analysis was performed in the same manner as in Example 3 except that the CYP3A4*16 mutant type probe was used.

The probe that was used is the CYP3A4*16 mutant type probe having the sequence below. The probe is a mutant type probe for a sense strand of the mutant type CYP3A4 gene. In the sequence below, the base that is underlined is a base that is complementary to the CYP3A4*16 mutant type sequence. The CYP3A4*16 mutant type probe was labeled with a fluorescent dye TAMRA at the 3' end.

CYP3A4*16 mutant type probe (U0-3TMR2)
(SEQ ID NO: 9)
5'-ctaCtgatcacatccatgctg-(TAMRA)-3'

Figure 9A:
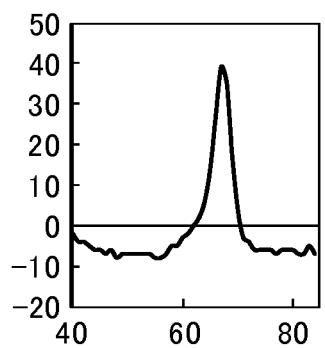
FIGS. 9A and 9B show melting curves of a sample according to Comparative Example 2.
Figure 9B:
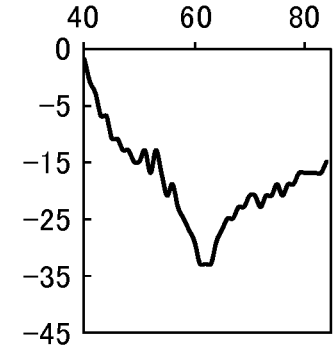

The results are illustrated in FIGS. 9(A) and 9(B). FIGS. 9(A) and 9(B) are graphs of the Tm analysis showing the change in the fluorescent intensity associated with temperature rise. In FIGS. 9(A) and 9(B), (A) shows the result for mt 100% and (B) shows the result for wt 100%. The horizontal axis shows the temperature (° C.) during measurement. The vertical axis shows the change in the fluorescent intensity (hereinafter, this is also referred to as "fluorescent change amount"), and the unit was "d fluorescence intensity increase amount/dt" (dF/dt).

As illustrated in FIG. 9(A), with respect to mt, the sample showed a peak only at the Tm value in relation to mt. On the other hand, as illustrated in FIG. 9(B), with respect to wt, the sample did not show a peak.

Example 4

In this Example, the CYP3A4*1B polymorphism, the CYP3A4*16 polymorphism, and the CYP3A5*3 polymorphism in the CYP3A4 gene were detected using the same reaction solution.

A purified genome, a plasmid, and pretreated whole blood were prepared as nucleic acid samples. The purified genome was prepared by a routine method from whole blood collected with an EDTA blood collection tube, and the purified genome adjusted to 400 copies/µL was used as a sample. As the plasmid, the CYP3A4*1B mutant type plasmid that includes a partial sequence of the CYP3A4 gene by insertion of the oligonucleotide having a sequence including the 366th to 651st bases in SEQ ID NO: 3 and the CYP3A4*16 mutant type plasmid that includes a partial sequence of the CYP3A4 gene by insertion of the oligonucleotide having a sequence including the 1st to 411th bases in SEQ ID NO: 2 were prepared. In the CYP3A4*1B mutant type plasmid, the 501st base in SEQ ID NO: 3 was a mutant type (g). In the CYP3A4*16 mutant type plasmid, the 201st base in SEQ ID NO: 2 was a mutant type (g). Each of the plasmids was adjusted to 2000 copies/µL, the adjusted plasmids were mixed with 0.5 of each, and the resultant was used as a sample. The pretreated whole blood was prepared as follows. That is, 10 µL of the whole blood that is the same as that used for preparation of the purified genome and 70 µL of the diluent 1 summarized in Table 2 were mixed to prepare a mixture, 100 µL of the mixture and 70 µL of the diluent 2 summarized in Table 2 were mixed, and then the resultant was heated at 95° C. for 10 minutes. In the nucleic acid to be detected contained in the whole blood, the CYP3A4*1B polymorphism is a homozygote of wild types, the CYP3A5*3 polymorphism is a heterozygote of a wild type and a mutant type, and the CYP3A4*16 polymorphism is a homozygote of wild types.

50 µL of PCR reaction mixtures respectively containing the aforementioned samples were prepared. Each of the PCR reaction mixtures was prepared by mixing the sample and the components of the PCR reaction solution summarized in the following Table 5 at the following concentrations. In the PCR reaction mixture, the concentration of the purified genome sample was $2 \times 10^6$ copies/L, the concentration of the plasmid sample was $2 \times 10^7$ copies/L, and the concentration of the whole blood sample was 5.3 mL/L. PCR and Tm analysis were performed in relation to the PCR reaction mixtures using a fully automated SNPs inspection device (product name: i-densy® IS-5310, produced by Arkray Inc.). Conditions for PCR were as follows. That is, after the PCR reaction mixture was treated at 95° C. for 1 minute, one cycle of treatment at 95° C. for 1 second and 58° C. for 30 seconds was repeated for 50 cycles. Further, the reaction mixture was treated at 95° C. for 1 second and 40° C. for 60 seconds. Thereafter, the reaction solution was heated from 40° C. to 75° C. at the temperature rise rate of 1° C./3 seconds to thereby perform Tm analysis by measurement of the change in the fluorescence intensity over time at a detection wavelength according to a fluorescent dye. Further, as a control, PCR and Tm analysis were performed in the same manner as described above except that the diluent 2 was used instead of the sample. The detection wavelength for PACIFIC BLUE was 445 to 480 nm, the detection wavelength for BODIPY FL was 520 to 555 nm, and the detection wavelength for TAMRA was 585 to 700 nm.

TABLE 5

1 × PCR reaction buffer
1.88 U Taq polymerase
1.5 mmol/L MgCl$_2$
0.2 mmol/L dNTP
0.5 µmol/L CYP3A4*1B F primer
0.25 µmol/L CYP3A4*1B R primer
0.25 µmol/L CYP3A5*3 F primer
0.5 µmol/L CYP3A5*3 R primer
2 µmol/L CYP3A4*16 F primer
4 µmol/L CYP3A4*16 R primer
0.2 µmol/L CYP3A4*1B probe
0.1 µmol/L CYP3A5*3 probe
0.4 µmol/L CYP3A4*16 probe The sequences of the CYP3A4*1B primer and the CYP3A4*1B probe are as follows.

```
(CYP3A4*1B primer)
F primer (CYP3A4-1B-F1)
                                    (SEQ ID NO: 26)
5'-ctgtaggtgtggcttgttgggatgaa-3'

R primer (CYP3A4-1B-R1)
                                    (SEQ ID NO: 27)
5'-ggagccattggcataaaatctattaaatcgc-3'

(CYP3A4*1B probe)
mutant type probe (3PB-CYP3A4*1B-R3)
                                    (SEQ ID NO: 12)
5'-taaatcgccGctctcctgccc-(PACIFIC BLUE)-3'
```

The sequences of the CYP3A4*16 primer and the CYP3A4*16 probe are as follows.

```
(CYP3A4*16 primer)
F primer (CYP3A4*16-F6 + CTAGA)
                                    (SEQ ID NO: 18)
5'-ctagaggagtgtgatagaaggtgatctagtaga-3'

R primer (U0-R3 + GACGA)
                                    (SEQ ID NO: 28)
5'-GACGAgagagaaagaatggatccaaa-3'

(CYP3A4*16 probe)
mutant type probe (3T-CYP3A4*16-MF1)
                                    (SEQ ID NO: 6)
5'-gatgtgatcaGtagc-(TAMRA)-3'
```

The sequences of the CYP3A5*3 primer and the CYP3A5*3 probe are as follows.

```
(CYP3A5*3 primer)
F primer (CYP3A5*3 F4)
                                    (SEQ ID NO: 14)
5'-cgtatgtaccacccagcttaacg-3'

R primer (CYP3A5*3 R4)
                                    (SEQ ID NO: 15)
5'-cacaggagccacccaagg-3'

(CYP3A5*3 probe)
mutant type probe (3FL-CYP3A5*3-mt-F1-21)
                                    (SEQ ID NO: 4)
5'-ttgtctttcaGtatctcttcc-(BODIPY FL)-3'
```

Figure 10A:
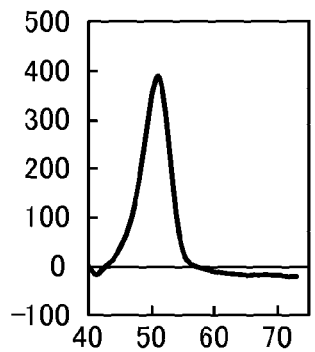
FIGS. 10A to 10C show melting curves of a sample according to Example 4 of the present invention.
Figure 10B:
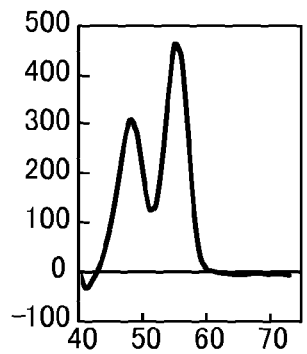
Figure 10C:
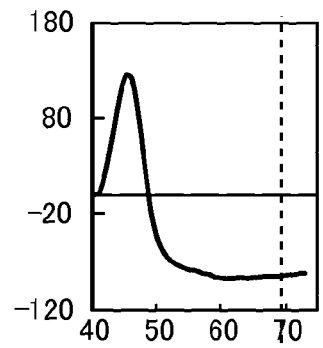
Figure 11A:
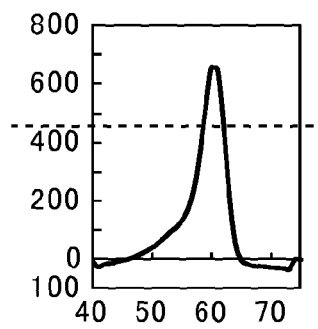
FIGS. 11A and 11B show melting curves of another sample according to Example 4 of the present invention.
Figure 11B:
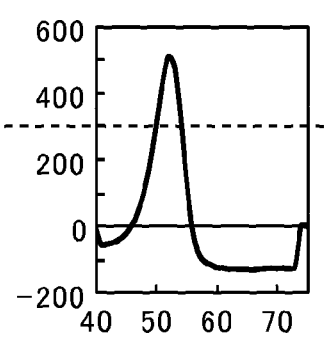
Figure 12A:
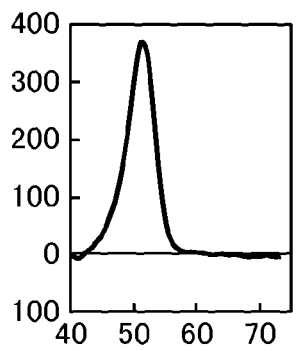
FIGS. 12A to 12C show melting curves of yet another sample according to Example 4 of the present invention.
Figure 12B:
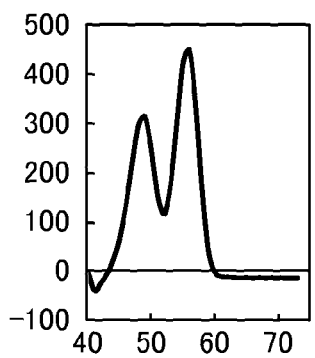
Figure 12C:
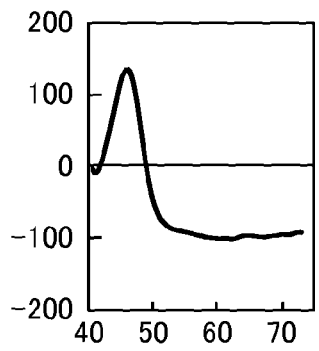

The results are illustrated in FIGS. 10(A) to 12(C). FIGS. 10(A) to 12(C) are graphs of the Tm analysis showing the change in the fluorescent intensity associated with temperature rise. FIGS. 10(A) to 10(C) show the results of the sample containing the purified genome, FIGS. 11(A) and 11(B) show the results of the sample containing the mixed plasmid, and FIGS. 12(A) to 12(C) show the results of the sample containing the pretreated whole blood. In FIGS. 10(A) to 10(C) and 12(A) to 12(C), (A) shows a melting curve with respect to the CYP3A4*1B mutant type probe, (B) shows a melting curve with respect to the CYP3A5*3 mutant type probe, and (C) shows a melting curve with respect to the CYP3A4*16 mutant type probe. In FIGS. 11(A) and 11(B), (A) shows a melting curve with respect to the CYP3A4*1B mutant type probe and (B) shows a melting curve with respect to the CYP3A4*16 mutant type probe. The horizontal axis shows the temperature (° C.) during measurement. The vertical axis shows the change in the fluorescent intensity (hereinafter, this is also referred to as "fluorescent change amount"), and the unit was "d fluorescence intensity increase amount/dt" (dF/dt). The Tm value of the CYP3A4*1B mutant type and the CYP3A4*1B mutant type probe is in proximity to 61° C., the Tm value of the CYP3A5*3 mutant type and the CYP3A5*3 mutant type probe is in proximity to 56° C., and the Tm value of the CYP3A4*16 mutant type and the CYP3A4*16 mutant type probe is in proximity to 53° C.

As illustrated in FIG. 10(A), with respect to the CYP3A4*1B polymorphism, the sample containing the purified genome that contains the CYP3A4*1B polymorphism as a homozygote of wild types showed a peak at a temperature lower than the Tm value in relation to a mutant type. As illustrated in FIG. 10(B), with respect to the CYP3A5*3 polymorphism, the sample containing the purified genome that contains the CYP3A5*3 polymorphism as a heterozygote of a wild type and a mutant type showed two peaks at the Tm value in relation to a mutant type and at a temperature lower than this Tm value. As illustrated in FIG. 10(C), with respect to the CYP3A4*16 polymorphism, the sample containing the purified genome that contains the CYP3A4*16 polymorphism as a homozygote of wild types showed a peak at a temperature lower than the Tm value in relation to a mutant type.

As illustrated in FIG. 11(A), with respect to the CYP3A4*1B polymorphism, the sample containing the mutant type plasmid showed a peak only at the Tm value in relation to a mutant type. As illustrated in 11(B), with respect to the CYP3A4*16 polymorphism, the sample containing the mutant type plasmid showed a peak only at the Tm value in relation to a mutant type. Since the plasmid sample does not contain the CYP3A5*3 polymorphism, the sample did not show a peak with respect to the CYP3A5*3 polymorphism.

As illustrated in FIG. 12(A), with respect to the CYP3A4*1B polymorphism, the sample containing the pretreated whole blood that contains the CYP3A4*1B polymorphism as a homozygote of wild types showed a peak at a temperature lower than the Tm value in relation to a mutant type. As illustrated in FIG. 12(B), with respect to the CYP3A5*3 polymorphism, the sample containing the pretreated whole blood that contains the CYP3A5*3 polymorphism as a heterozygote of a wild type and a mutant type showed two peaks at the Tm value in relation to a mutant type and at a temperature lower than this Tm value. As illustrated in FIG. 12(C), with respect to the CYP3A4*16 polymorphism, the sample containing the pretreated whole blood that contains the CYP3A4*16 polymorphism as a homozygote of wild types showed a peak at a temperature lower than the Tm value in relation to a mutant type.

Example 5

In this Example, Tm analysis was respectively performed in relation to a wild-type artificial nucleic acid and a mutant-type artificial nucleic acid to detect the polymorphism (CYP3A4*1B) in the CYP3A gene using a probe that hybridizes to a sense strand.

As artificial nucleic acids of sense strand, a wild type artificial nucleic acid (WT 1) and mutant type artificial nucleic acids (mt 1-1 and mt 1-2) that correspond to the 482nd to 521st bases in SEQ ID NO: 3 as illustrated in the sequences below were prepared. In the sequences below, the underlined bases correspond to the 501st base in SEQ ID NO: 3. In the sequences below, the bases in lower case are substituted with bases that are different from those of SEQ ID NO: 3. The respective artificial nucleic acids were adjusted to 0.1 µmol/L.

```
WT 1 (CYP3A4*1B-WT-F)
                                          (SEQ ID NO: 29)
AGCCATAGAGACAAGGGCAAGAGAGgGGCGATTTAATAGA mt 1-1 (CYP3A4*1B-mt1-F)
                                          (SEQ ID NO: 30)
AGCCATAGAGACAAGGGCAGGAGAGaGGCGATTTAATAGA mt 1-2 (CYP3A4*1B-mt2-F)
                                          (SEQ ID NO: 31)
AGCCATAGAGACAAGGGCAGGAGAGgGGCGATTTAATAGA
```

50 µL of reaction mixtures respectively containing the aforementioned artificial nucleic acids were prepared. Each of the reaction mixtures was prepared by mixing the components of the reaction solution summarized in the following Table 6 at the following concentrations. Tm analysis was performed in relation to the reaction mixtures using a fully automated SNPs inspection device (product name: i-densy® IS-5310, produced by Arkray Inc.). Conditions for Tm analysis were as follows. That is, the reaction solution was treated at 95° C. for 1 second and 40° C. for 60 seconds. Thereafter, the reaction solution was heated from 40° C. to 75° C. at the temperature rise rate of 1° C./3 seconds to thereby perform Tm analysis by measurement of the change in the fluorescence intensity over time at a detection wavelength according to a fluorescent dye. The detection wavelength for PACIFIC BLUE was 445 to 480 nm.

TABLE 6

| |
|---|
| 1 × reaction buffer |
| 1.88 U Taq polymerase |
| 1.5 mmol/L MgCl$_2$ |
| 0.2 mmol/L dNTP |
| 0.2 mmol/L probe |
| 0.2 mmol/L wild-type artificial nucleic acid (WT 1) |
| 0.2 mmol/L mutant-type artificial nucleic acid (mt 1-1 or mt 1-2) |

The probe that was used is the CYP3A4*1B mutant type probe having the sequence below. The probe is a mutant type probe for a sense strand of the mutant type CYP3A4 gene. In the sequence below, the base that is underlined is a base that is complementary to the CYP3A4*1B mutant type sequence.

```
CYP3A4*1B probe (3PB-CYP3A4*1B-R3)
                                          (SEQ ID NO: 12)
5'-taaatcgccGctctcctgccc-(PACIFIC BLUE)-3'
```

Comparative Example 3

Comparative Example 3-1

In this Comparative Example, Tm analysis was respectively performed in relation to a wild-type artificial nucleic acid and a mutant-type artificial nucleic acid to detect the polymorphism (CYP3A4*1B) in the CYP3A gene using a probe that hybridizes to a sense strand.

The CYP3A4*1B probe that was used is the probe having the sequence below. The probe is a wild type probe for a sense strand of the wild type CYP3A4 gene. In the sequence below, the base that is underlined is a base that is complementary to the CYP3A4*1B mutant type sequence.

```
      probe 3-1 (5PB-CYP3A4*1B-R1)
                                  (SEQ ID NO: 32)
      5'-(PACIFIC BLUE)-ctctcttgcccttgt-3'
```

Tm analysis was performed in the same manner as in Example 5 except that the probe 3-1 was used as the CYP3A4*1B probe.

Comparative Example 3-2

In this Comparative Example, Tm analysis was respectively performed in relation to a wild-type artificial nucleic acid and a mutant-type artificial nucleic acid to detect the polymorphism (CYP3A4*1B) in the CYP3A gene using a probe that hybridizes to an antisense strand.

As artificial nucleic acids of antisense strand, a wild type artificial nucleic acid (WT 2) and mutant type artificial nucleic acids (mt 2-1 and mt 2-2) that are complementary to the 482nd to 521st bases in SEQ ID NO: 3 as illustrated in the sequences below were prepared. In the sequences below, the underlined bases correspond to the 501st base in SEQ ID NO: 3. The respective artificial nucleic acids were adjusted to 0.1 μmol/L.

```
      WT 2 (CYP3A4*1B-WT-R)
                                  (SEQ ID NO: 33)
      tctattaaatcgccCctctcttgcccttgtctctatggct mt 2-1 (CYP3A4*1B-mt1-R)
                                  (SEQ ID NO: 34)
      tctattaaatcgccTctctcctgcccttgtctctatggct mt 2-2 (CYP3A4*1B-mt2-R)
                                  (SEQ ID NO: 35)
      tctattaaatcgccCactcctgcccttgtactatggct
```

The CYP3A4*1B probe that was used is the probe 2-2 having the sequence below. The probe is a wild type probe for an antisense strand of the wild type CYP3A4 gene. In the sequence below, the base that is underlined is a base that corresponds to the CYP3A4*1B wild type.

```
      probe 2-2 (5PB-CYP3A4*1B-F1)
                                  (SEQ ID NO: 36)
      5'-(PACIFIC BLUE)-CAAGGGCAAGAGAGAG-3'
```

Tm analysis was performed in the same manner as in Example 5 except that the WT 2 was used as the wild type artificial nucleic acid, the mt 2-1 or the mt 2-2 was used as the mutant type artificial nucleic acid, and the probe 2-2 was used as the CYP3A4*1B probe.

Figure 13A:
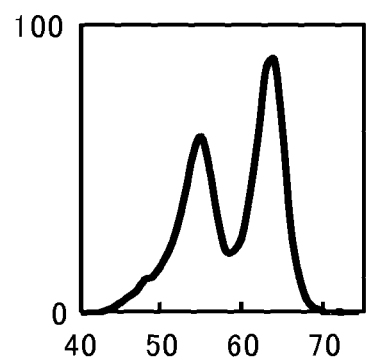
FIGS. 13A and 13B show melting curves of a sample according to Example 5 of the present invention.
Figure 13B:
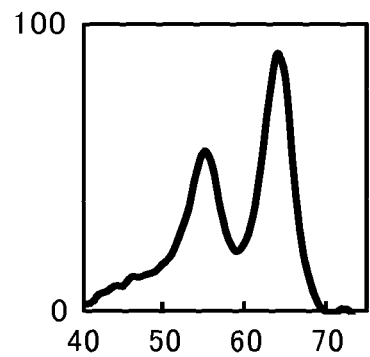
Figure 14:
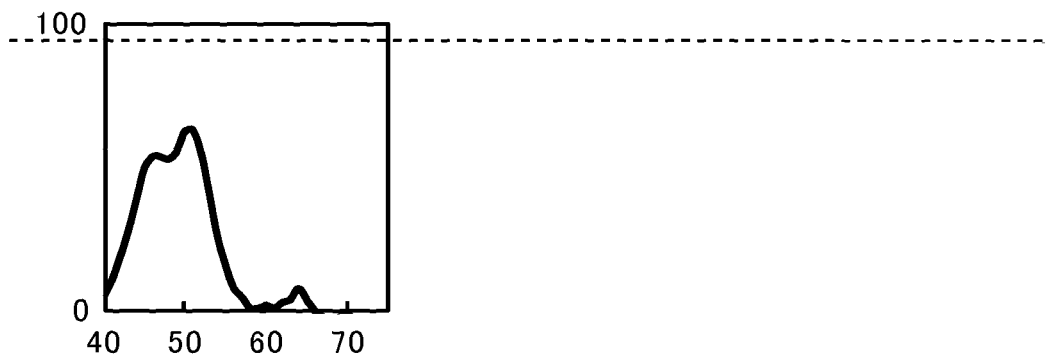
FIG. 14 shows a melting curve of a sample according to Comparative Example 3-1.
Figure 15:
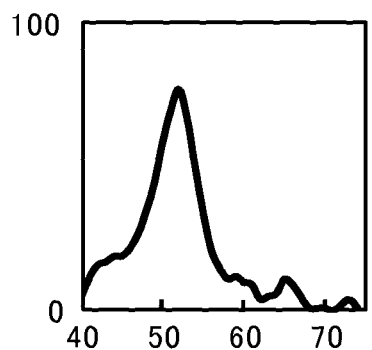
FIG. 15 shows a melting curve of a sample according to Comparative Example 3-2.

The results are illustrated in FIGS. 13(A) to 15. FIGS. 13(A) to 15 are graphs of the Tm analysis showing the change in the fluorescent intensity associated with temperature rise. FIGS. 13(A) and 13(B) show the results of Example 5, FIG. 14 shows the result of Comparative Example 3-1, and FIG. 15 shows the result of Comparative Example 3-2. The horizontal axis shows the temperature (° C.) during measurement. The vertical axis shows the change in the fluorescent intensity (hereinafter, this is also referred to as "fluorescent change amount"), and the unit was "d fluorescence intensity increase amount/dt" (dF/dt).

As illustrated in FIGS. 13(A) and 13(B), in Example 5, in the case where the combination of WT 1 and mt 1-1 or the combination of WT 1 and mt 1-2 was added to the PCR reaction solution, peaks for WT 1 (55° C.) and mt 1-1 (64° C.) or mt 1-2 (64° C.) were observed. On the other hand, as illustrated in FIG. 14, in Comparative Example 3-1, in the case where the combination of WT 1 and mt 1-1 was added to the PCR reaction solution, a peak for WT 1 overlapped with a peak for mt 1-1; and in the case where the combination of WT 1 and mt 1-2 was added to the PCR reaction solution, a peak for WT 1 and a peak for mt 1-2 were not observed. Further, as illustrated in FIG. 15, in Comparative Example 3-2, in the case where the combination of WT 2 and mt 2-2 was added to the PCR reaction solution, a peak for WT 2 overlapped with a peak for mt 2-2; and in the case where the combination of WT 2 and mt 2-1 was added to the PCR reaction solution, a peak for WT 2 and a peak for mt 2-1 were not observed.

In this manner, it became evident that a simple detection of polymorphism in the CYP3A gene with high sensitivity can be performed according to the present invention.

According to the polymorphism detection method of the present invention, a probe for detecting polymorphism that enables a simple detection of polymorphism in the CYP3A gene with high sensitivity and a method of detecting polymorphism using the probe can be provided. Further, the present invention can provide a method of evaluating a drug efficacy using the method of detecting polymorphism. Furthermore, the present invention can provide a reagent kit for detecting polymorphism using the probe for detecting polymorphism.

The invention may be embodied in other forms without departing from the spirit or essential characteristics thereof. The embodiments disclosed in this application are to be considered in all respects as illustrative and not limiting. The scope of the invention is indicated by the appended claims rather than by the foregoing description, and all changes which come within the meaning and range of equivalency of the claims are intended to be embraced therein.

The invention claimed is:

1. A probe composition comprising:
   (i) a first probe comprising a label and an oligonucleotide sequence, wherein the oligonucleotide sequence of the first probe consists of an oligonucleotide selected from the group consisting of SEQ ID NO: 4, 5 or 37;
   (ii) a second probe comprising a label and an oligonucleotide sequence, wherein the oligonucleotide sequence of the second probe consists of an oligonucleotide selected from the group consisting of SEQ ID NO: 6, 7, 38, 8, 39, 40, 10, 11, 41, 42, 43 or 44; and
   (iii) a third probe comprising a label and an oligonucleotide sequence, wherein the oligonucleotide sequence of the third probe consists of an oligonucleotide selected from the group consisting of SEQ ID NO: 12, 13 or 45;
   wherein the nucleotide base at the first, second or third position from the 3' end of each oligonucleotide sequence is labeled with a fluorescent dye.

2. The probe composition according to claim 1, wherein the nucleotide base at the 3' end of each oligonucleotide sequence is labeled with a fluorescent dye.

3. The probe composition of claim 1, wherein the labels of the first, second and third probes emit fluorescence when not hybridized to their target sequences, and the fluorescence intensities when hybridized to the target sequences are smaller than the fluorescence intensities when not hybridized to the target sequences.

4. The probe composition of claim 1, wherein:
   (i) the oligonucleotide sequence of the first probe consists of SEQ ID NO: 37;
   (ii) the oligonucleotide sequence of the second probe consists of SEQ ID NO: 38, 39, 41 or 43; or
   (iii) the oligonucleotide sequence of the third probe consists of SEQ ID NO: 45.

5. The probe composition of claim 1, wherein:
   (i) the oligonucleotide sequence of the first probe consists of SEQ ID NO: 4;
   (ii) the oligonucleotide sequence of the second probe consists of SEQ ID NO: 6, 8, 10 or 44; or
   (iii) the oligonucleotide sequence of the third probe consists of SEQ ID NO: 12.

6. A method of detecting polymorphism in a CYP3A gene in a sample using the probe composition according to claim 1, comprising:
   adding to the sample the probe composition according to claim 1;
   obtaining a melting curve for the probe; and
   determining the melting temperature of the probe from the melting curve, wherein the melting temperature indicates the presence of the polymorphism in the CYP3A gene.

7. The method of claim 6, further comprising:
   contacting the probe composition with a single-stranded nucleic acid in a sample and hybridizing the probe composition and the single-stranded nucleic acid to obtain a hybrid;
   measuring a change in a fluorescent signal based on dissociation of the hybrid by changing the temperature of the sample comprising the hybrid in order to dissociate the hybrid;
   determining a Tm value which is a temperature at which the hybrid dissociates based on the change in the fluorescent signal; and
   determining whether or not polymorphism of the CYP3A gene is present in the single-stranded nucleic acid in the sample based on the Tm value.

8. The method of claim 7, further comprising amplifying the nucleic acid before or at the same time as contacting the probe composition with a single-stranded nucleic acid in a sample and hybridizing the probe composition and the single-stranded nucleic acid to obtain a hybrid.

9. A method of evaluating a drug efficacy or tolerance, the method comprising:
   detecting a polymorphism in the CYP3A gene by the method of claim 6; and evaluating tolerance to the drug or the efficacy of the drug based on the presence or absence of the polymorphism.

10. A reagent kit for detecting polymorphism in the CYP3A gene, the reagent kit comprising the probe composition of claim 1.

11. The reagent kit of claim 10, further comprising a primer for amplifying a sequence to which at least one of the first, second, and third probes hybridizes.

12. The reagent kit of claim 10, further comprising first, second and third primers for amplifying sequences to which the first, second, and third probes hybridize, respectively.

13. The reagent kit of claim 11, wherein the primer:
amplifies a region including a sequence to which the first probe hybridizes;
has a sequence comprising the $322^{nd}$ to the $344^{th}$ bases of SEQ ID NO: 1;
and has a length of from 23 bases to 50 bases.

14. The reagent kit of claim 11, wherein the primer:
amplifies a region including a sequence to which the second probe hybridizes; and
(i) has a sequence comprising the complementary strand of the $446^{th}$ to the $463^{rd}$ bases of SEQ ID NO: 1, and has a length of from 18 bases to 50 bases;
(ii) has a sequence comprising the $118^{th}$ to the $137^{th}$ bases of SEQ ID NO: 2, and has a length of from 20 bases to 50 bases; or
(iii) has a sequence comprising the $22^{nd}$ to the $49^{th}$ bases of SEQ ID NO: 2, and has a length of from 28 bases to 50 bases.

15. The reagent kit of claim 11, wherein the primer:
amplifies a region including a sequence to which the third probe hybridizes,;
has a sequence comprising the complementary strand of the $292^{nd}$ to the $312^{th}$ bases of SEQ ID NO: 2; and
has a length of from 21 bases to 50 bases.

16. The reagent kit of claim 12, wherein:
(a) the first primer amplifies a region including a sequence to which the first probe hybridizes; has a sequence comprising the $322^{nd}$ to the $344^{th}$ bases of SEQ ID NO: 1; and has a length of from 23 bases to 50 bases;
(b) the second primer amplifies a region including a sequence to which the second probe hybridizes; and
(i) has a sequence comprising the complementary strand of the $446^{th}$ to the $463^{rd}$ bases of SEQ ID NO: 1, and has a length of from 18 bases to 50 bases;
(ii) has a sequence comprising the $118^{th}$ to the $137^{th}$ bases of SEQ ID NO: 2, and has a length of from 20 bases to 50 bases; or
(iii) has a sequence comprising the $22^{nd}$ to the $49^{th}$ bases of SEQ ID NO: 2, and has a length of from 28 bases to 50 bases; and
(c) amplifies a region including a sequence to which the third probe hybridizes; has a sequence comprising the complementary strand of the $292^{nd}$ to the $312^{th}$ bases of SEQ ID NO: 2; and has a length of from 21 bases to 50 bases.

17. The probe composition of claim 1, wherein:
(i) the oligonucleotide sequence of the first probe consists of SEQ ID NO: 37;
(ii) the oligonucleotide sequence of the second probe consists of SEQ ID NO: 38, 39, 41 or 43; and
(iii) the oligonucleotide sequence of the third probe consists of SEQ ID NO: 45.

18. The probe composition of claim 1, wherein:
(i) the oligonucleotide sequence of the first probe consists of SEQ ID NO: 4;
(ii) the oligonucleotide sequence of the second probe consists of SEQ ID NO: 6, 8, 10 or 44; and
(iii) the oligonucleotide sequence of the third probe consists of SEQ ID NO: 12.

19. The probe composition of claim 1, wherein:
(i) the oligonucleotide sequence of the first probe consists of SEQ ID NO: 4;
(ii) the oligonucleotide sequence of the second probe consists of SEQ ID NO: 6, 8, or 44; and
(iii) the oligonucleotide sequence of the third probe consists of SEQ ID NO: 12.

20. The probe composition of claim 1, wherein the oligonucleotide sequence of the second probe consists of SEQ ID NO: 6, 7, 38, 10, 11, 41, 42, 43 or 44.

21. The probe composition of claim 20, wherein
(i) the oligonucleotide sequence of the first probe consists of SEQ ID NO: 4;
(ii) the oligonucleotide sequence of the second probe consists of SEQ ID NO: 6 or 44; and
(iii) the oligonucleotide sequence of the third probe consists of SEQ ID NO: 12.

* * * * *